(12) United States Patent
Vidal Juan et al.

(10) Patent No.: US 7,504,398 B2
(45) Date of Patent: Mar. 17, 2009

(54) SUBSTITUTED-4-(PYRROLO PYRIMIDIN-6-YL)BENZENESULPHONAMIDE DERIVATIVES

(75) Inventors: Bernat Vidal Juan, Barcelona (ES); Cristina Esteve Trias, Barcelona (ES)

(73) Assignee: Laboratorios Almirall S.A., Barcelona (ES)

( * ) Notice: Subject to any disclaimer, the term of this patent is extended or adjusted under 35 U.S.C. 154(b) by 152 days.

(21) Appl. No.: 10/509,280

(22) PCT Filed: Apr. 1, 2003

(86) PCT No.: PCT/EP03/03378

§ 371 (c)(1), (2), (4) Date: May 5, 2005

(87) PCT Pub. No.: WO03/082873

PCT Pub. Date: Oct. 9, 2003

(65) Prior Publication Data

US 2005/0261248 A1  Nov. 24, 2005

(30) Foreign Application Priority Data

Apr. 1, 2002  (ES)  ............... 200200752

(51) Int. Cl.
C07D 487/04 (2006.01)
A61K 31/519 (2006.01)
A61K 31/661 (2006.01)
C07F 9/38 (2006.01)
C07F 9/40 (2006.01)
A61P 35/04 (2006.01)
A61P 25/16 (2006.01)
A61P 25/28 (2006.01)
A61P 11/06 (2006.01)

(52) U.S. Cl. ............... 514/252.16; 514/265.1; 514/81; 544/280; 544/244

(58) Field of Classification Search ............... 544/280, 544/244; 514/265.1, 81, 252.16
See application file for complete search history.

(56) References Cited

FOREIGN PATENT DOCUMENTS

| EP | 0 092 398 A1 | 3/1987 |
|---|---|---|
| EP | 0480659 | 4/1992 |
| WO | WO 86/02551 | 5/1986 |
| WO | WO 01 94350 A2 | 12/2001 |
| WO | WO 03 000694 | 1/2003 |

OTHER PUBLICATIONS

Palmer Trends in Pharmacological Sciences 23(9) 426-433 Sep. 2002.*

Bettina Grahner, et al., "Synthesis and structure-activity relationships of deazaxanthines: analogs of potent $A_1$- and $A_2$-adenosine receptor antagonists," Journal of Medicinal Chemistry, 37(10):1526-1534 (1994).
Igor Feoktistov, et al., "Adenosine $A_{2B}$ receptors," Pharmacological Reviews, 49(4):381-402 (1997).
Kenneth A. Jacobson, et al., "Functionalized congeners of 1,3-dialkylxanthines: preparation of analogues with high affinity for adenosine receptors," Journal of Medicinal Chemistry, 28(9):1334-1340 (1985).
Junich Shimada, et al., "8-polycycloakly-1,3-dipropylxanthines as potent and selective antagonists for $A_1$-adenosine receptors," Journal of Medicinal Chemistry, 35(5):924-930 (1992).
Kim Yong-Chul, et al., "Anilide derivatives of an 8-phenylxanthine carboxylic congener are highly potent and selective antagonists at human $A_{2B}$ adenosine receptors," Journal of Medicinal Chemistry, 43(6):1165-1172 (2000).
Kim Yong-Chul, et al., "Acyl-hydrazide derivatives of a xanthine carboxylic congener (XCC) as selective antagonists at human $A_{2B}$ adenosine receptors," Drug Development Research, 47(4):178-188 (1999).
Yoneda Fumio, et al., Syntheses and properties of 3-hydroxy-4,6-dimethylpyrrolo[3,2-d]pyrimidine-5-7(4H,6H)-dione (9-hydroxy-9-deazatheophylline) derivatives,: Chem. Pharma Bull, 30(9):3187-1396 (1982).
Helmut Fenner, et al., "Pyrrolo [3, 2 -d] pyrimidine aus pyrimido [4.5-b][1.4] thiazinen," Terahedron Letters, 44:4185-4188 (1971).
Shigeo Senda, et al., "Pyrimidine derivatives and related compounds. XXIX. Photoreductive cyclization of 5-nitro-6-styryl(or anilino)uralic derivatives to pyrrolo[3,2-d]pyrimidine and alloxazine derivatives," Chem. Pharma. Bull, 25(4):563-568 (1977).
Hermut Fenner, et al., "9-deazapurine aus pyrimido[4.5-b] [1.4] thiazinen," Arch. Pharma, 311(2):153-161 (1978).
Robert F. Burns, et al., "Adenosine receptors in brain membranes: binding of $N^6$cyclohexyl[$^3$H]adenosine and 1,3-diethyl-8-[$^3$H]phenylxantine," Proc. Natl. Acad. Sci. USA, 77(9):5547-555 (1980).
Cristina Esteve, et al, "New pyrrolopyrimidin-6-yl benzenesulfonamides: potent $A_{2B}$ adenosine receptor antagonists," Bioorganic & Medicinal Chemistry Letters, 16:3642-3645 (2006).
Office Action from U.S. Appl. No. 10/481,728, dated Feb. 26, 2007.

* cited by examiner

Primary Examiner—Brenda Coleman
Assistant Examiner—Susanna Moore
(74) Attorney, Agent, or Firm—Finnegan, Henderson, Farabow, Garrett & Dunner, LLP

(57) ABSTRACT

This invention is directed to selective antagonists of $A_{2A}$ and/or $A_{2B}$ adenosine receptors having the general formula (I); to processes for their preparation; to pharmaceutical compositions comprising them; and to their use in therapy.

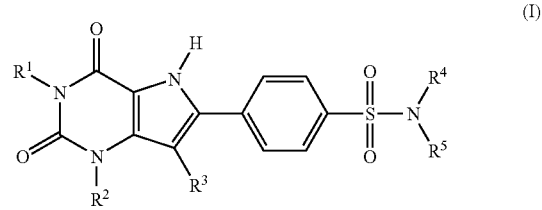

(I)

14 Claims, No Drawings

SUBSTITUTED-4-(PYRROLO PYRIMIDIN-6-YL)BENZENESULPHONAMIDE DERIVATIVES

This application is a national stage filing under 35 U.S.C. § 371 of International Application No. PCT/EP03/03378, filed on Apr. 1, 2003. This application claims the benefit of priority under 35 U.S.C. § 119 to Spanish Patent Application No. P200200752 filed on Apr. 1, 2002.

The present invention relates to new antagonists of $A_{2A}$ and $A_{2B}$ adenosine receptors. These compounds are useful in the treatment, prevention or suppression of diseases and disorders known to be susceptible of being improved by antagonism of $A_{2A}$ and/or $A_{2B}$ adenosine receptors, such as Parkinson's disease, asthma, allergic diseases, inflammation, atherosclerosis, hypertension, gastrointestinal tract disorders, cell proliferation disorders and autoimmune diseases.

Adenosine regulates several physiological functions through specific cell membrane receptors, which are members of the G-protein coupled receptor family. Four distinct adenosine receptors have been identified and classified: $A_1$, $A_{2A}$, $A_{2B}$ and $A_3$.

$A_{2A}$ adenosine receptors are mainly found in the brain (striatum, nucleus accumbens and olfactory bulb), platelets, leukocytes, spleen and thymus (see Fredholm et al. *Pharmacol Rev.* 2001, 53 (4), 527-552). Adenosine $A_{2A}$ receptors modulate the release of GABA in the striatum. Thus, $A_{2A}$ receptor antagonists are a useful alternative for the treatment for Parkinson's disease (Mally, J. and Stone, T. W., *CNS Drugs,* 1998, 10, 311-320) and for other neurodegenerative diseases. The pharmacology of $A_{2A}$ adenosine receptors has been reviewed by Ongini et al. in *Trends Pharmacol Sci.* 1996, 17(10), 364-372.

The $A_{2B}$ adenosine receptor subtype (see Feoktistov, I., Biaggioni, I. *Pharmacol. Rev.* 1997, 49, 381-402) has been identified in a variety of human and murine tissues and is involved in the regulation of vascular tone, smooth muscle growth, angiogenesis, hepatic glucose production, bowel movement, intestinal secretion, and mast cell degranulation.

In view of the physiological effects mediated by adenosine receptor activation, several $A_{2A}$ and/or $A_{2B}$ receptor antagonists have been recentiy disclosed for the treatment or prevention of Parkinson's disease, Alzheimer disease, Huntington chorea, Wilson's disease, asthma, bronchoconstriction, allergic diseases, hypertension, atherosclerosis, reperfusion injury, myocardial ischemia, retinopathy, inflammation, gastrointestinal tract disorders, cell proliferation diseases and/or diabetes mellitus. See for example WO 01/16134, WO 01/02400, WO 01/80893 or WO 00/73307.

It has now been found that certain 4-(pyrrolopyrimidin-6-yl)benzenesulphonamide derivatives are new potent and selective antagonists of $A_{2A}$ and $A_{2B}$ adenosine receptors and can therefore be used in the treatment or prevention of these diseases.

Further objectives of the present invention are to provide a method for preparing said compounds; pharmaceutical compositions comprising an effective amount of said compounds; the use of the compounds in the manufacture of a medicament for the treatment of pathological conditions or diseases susceptible of being improved by antagonism of $A_{2A}$ and/or $A_{2B}$ adenosine receptors; and methods of treatment of pathological conditions or diseases susceptible to amelioration by antagonism of $A_{2A}$ and/or $A_{2B}$ adenosine receptors comprising the administration of the compounds of the invention to a subject in need of treatment.

Thus, the present invention is directed to new 6-(4-aminosulphonylphenyl)-1,5-dihydropyrrolo[3,2-d]pyrimidine-2,4-dione derivatives of formula (I)

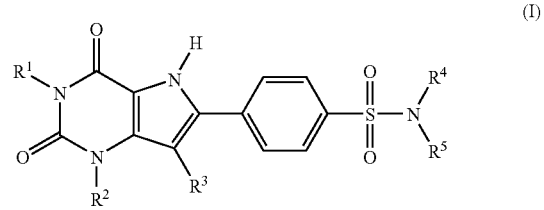

wherein
$R^1$ and $R^2$ each independently represent:
a hydrogen atom;
a hydrocarbon chain selected from an alkyl, alkenyl or alkynyl group, which is optionally substituted by one or more, for example 1, 2, 3 or 4, substituents selected from halogen, hydroxy, alkoxy, alkylthio, amino, monoalkylamino, dialkylamino, cyano, oxo, hydroxycarbonyl, alkoxycarbonyl, acylamino, carbamoyl, alkylcarbamoyl, dihydroxyphosphoryloxy or dialkoxyphosphoryloxy groups;
or a group of formula

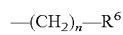

wherein n is an integer from 0 to 4 and $R^6$ represents a 3- to 7-membered aromatic or non-aromatic cyclic group containing from 0 to 4 heteroatoms selected from N, O and S, which is optionally bridged and/or fused to another 3- to 7-membered aromatic or non-aromatic cyclic group containing from 0 to 4 heteroatoms selected from N, O and S;
the cyclic groups in the moiety $R^6$ being optionally substituted by one or more, for example 1, 2, 3 or 4, $R^7$ substituents selected from halogen, alkyl, alkenyl, alkynyl, aryl, arylalkyl, cycloalkyl, heteroaryl, heteroarylalkyl, heterocydyl, hydroxy, alkylenedioxy, alkoxy, alkylthio, amino, monoalkylamino, dialkylamino, nitro, cyano, oxo, hydroxycarbonyl, alkoxycarbonyl, acylamino, carbamoyl, alkylcarbamoyl, dihydroxyphosphoryloxy and dialkoxyphosphoryloxy groups;
the hydrocarbon chains and the cyclic moieties of these $R^7$ substituents being optionally substituted by one or more, for example 1, 2, 3 or 4, further $R^8$ substituents selected from halogen, hydroxy, oxo, cyano, alkyl, difluoromethyl, trifluoromethyl, alkoxy, alkylenedioxy, alkylthio, acylamino, carbamoyl, alkylcarbamoyl, dihydroxyphosphoryloxy, dialkoxyphosphoryloxy, hydroxyalkoxy, phenyl, alkoxycarbonyl, amino, monoalkylamino, dialkylamino and hydroxycarbonyl groups;
$R^3$ represents a hydrogen or halogen atom, or a nitro, alkoxycarbonyl or alkyl group; the alkyl group being optionally substituted by one or more, for example 1, 2, 3 or 4, substituents selected from hydroxy, alkoxy, alkylthio, amino, monoalkylamino, dialkylamino, hydroxycarbonyl, alkoxycarbonyl, acylamino, carbamoyl or alkylcarbamoyl groups;
$R^4$ and $R^5$ are the same or different, each independently representing:
hydrogen;
a group of formula —$(CH_2)_n$—$R^6$, wherein n is an integer from 0 to 4; and $R^6$ is as defined above and is optionally substituted by one or more, for example 1, 2, 3 or 4, $R^7$ substituents, wherein $R^7$ is as defined above and is optionally substituted by one or more, for example 1, 2, 3 or 4, further $R^8$ substituents. wherein $R^8$ is as defined above;

or a hydrocarbon chain selected from alkyl, alkenyl or alkynyl, which is optionally substituted by one or more, for example 1, 2, 3 or 4, substituents selected from —$(CH_2)_n$—$R^6$, —O—$(CH_2)_n$—$R^6$, —S—$(CH_2)_n$—$R^6$, —NH—$(CH_2)_n$—$R^6$, hydroxy, oxo, halogen, alkoxy, alkylthio, amino, monoalkylamino, and dialkylamino groups; the alkyl chains in the alkoxy, alkylthio, monoalkylamino and dialkylamino substituents being optionally substituted by one or more, for example 1, 2, 3 or 4, further substituents selected from —$(CH_2)_n$—$R^6$, hydroxy, oxo, halogen, alkoxy, alkylthio, amino, monoalkylamino and dialkylamino groups; and wherein each n is independently an integer from 0 to 4 and each $R^6$ is as defined above and is optionally substituted by one or more, for example 1, 2, 3 or 4, $R^7$ substituents, wherein $R^7$ is as defined above and is optionally substituted by one or more, for example 1, 2, 3 or 4, further $R^8$ substituents, wherein $R^8$ is as defined above;

or, alternatively, $R^4$ and $R^5$, together with the nitrogen atom to which they are attached, form a 3- to 7-membered aromatic or non-aromatic cyclic group comprising from 1 to 4 heteroatoms selected from N, O and S, which is optionally bridged and/or fused to another 3- to 7-membered aromatic or non-aromatic cyclic group containing from 0 to 4. heteroatoms selected from N, O and S; the cyclic groups being optionally substituted by one or more, for example 1, 2, 3 or 4, substituents selected from —$(CH_2)_n$—$R^6$ and $R^7$; the hydrocarbon chains and the cyclic moieties of the $R^7$ substituents being optionally substituted by one or more, for example 1, 2, 3 or 4, further substituents selected from —$(CH_2)_n$—$R^6$ and $R^8$; and the alkyl chains in the $R^5$ substituents being optionally substituted by one or more, for example 1, 2, 3 or 4, further substitutents selected from —$(CH_2)_n$—$R^6$, hydroxy, halogen, alkoxy, alkylthio, amino, monoalkylamino and dialkylamino groups; wherein each of the $R^6$ substituents is optionallly substitued by one or more, for example 1, 2, 3 or 4, $R^7$ substituents and each of these $R^7$ substituents is optionally substituted by one or more, for example 1, 2, 3 or 4, $R^8$ substituents; and wherein each n, $R_6$, $R^7$ and $R^8$ is as defined above.

or an N-oxide or a pharmaceutically acceptable salt thereof.

As used herein, a hydrocarbon chain is a straight or branched non-cylic sequence of carbon atoms covalently linked by single, double or triple bonds, and substituted by hydrogen atoms, for example straight or branched alkyl, alkenyl or alkynyl groups, moieties or chains. Typically, the hydrocarbon chains contain from 1 to 10 carbon atoms. As used herein, an alkyl, alkenyl or alkynyl group or moiety is a straight or branched group or moiety. Typically it is a $C_1$-$C_{10}$ group or moiety, for example a $C_1$-$C_6$ group or moiety, preferably a $C_1$-$C_4$ group or moiety. Examples include methyl, ethyl. i-propyl, n-propyl, n-butyl, t-butyl, allyl, 2-propenyl and 3-butynyl. Where a group contains two or more alkyl, alkenyl or alkynyl moieties, these moieties may be the same or different. When an alkyl, alkenyl or alkynyl chain, group or moiety carries 2 or more substituents, the substituents may be the same or different.

As used herein, an alkylene group or moiety is a divalent alkyl moiety typically having from 1 to 6, for example from 1 to 4, carbon atoms. Examples of $C_1$-$C_4$ alkylene groups include methylene, ethylene, propylene and butylene groups. When an alkylene or alkylenedioxy group is present as a substituent on another group it shall be deemed to be a single substituent, rather than a group formed by two substituents.

As used herein, the alkyl chains present in the arylalkyl, heteroarylalkyl, alkoxy, alkylthio, monoalkylamino, dialkylamino, hydroxyalkoxy, alkoxycarbonyl, alkylcarbamoyl, alkylenedioxy and dialkoxyphosphoryloxy groups are typically straight or branched alkyl chains containing from 1 to 6 carbon atoms.

As used herein, an acyl group or moiety typically has from 2 to 7 carbon atoms. Thus, it is typically a group of formula —COR wherein R is a hydrocarbon chain group having from 1 to 6 carbon atoms. Preferably, it is a group of formula —COR wherein R is a $C_1$-$C_6$ alkyl group.

As used herein, an aryl group or moiety is typically a $C_6$-$C_{10}$ aryl group or moiety such as phenyl or naphthyl. Phenyl is preferred. When an aryl group or moiety carries 2 or more substituents, the substituents may be the same or different.

As used herein, a heteroaryl group or moiety is typically a 5- to 10-membered aromatic ring, such as a 5- or 6-membered ring, containing at least one heteroatom selected from O, S and N. Examples include pyridyl, pyrazinyl, pyrimidinyl, pyridazinyl, furanyl, oxadiazolyl, oxazolyl, imidazolyl, thiazolyl, thiadiazolyl, thienyl, pyrazolidinyl, pyrrolyl and pyrazolyl groups. Oxadiazolyl, oxazolyl, pyridyl, pyrrolyl, imidazolyl, thiazolyl, thiadiazolyl, furanyl, thienyl, pyrazinyl and pyrimidinyl groups are preferred. When a heteroaryl group or moiety carries 2 or more substituents, the substituents may be the same or different.

As used herein, a cycloalkyl group typically has from 3 to 6 carbon atoms. Examples include cyclopropyl, cyclobutyl, cyclopentyl and cyclohexyl. It is preferably cyclopropyl, cyclopentyl or cyclohexyl. When a cycloalkyl group carries 2 or more substituents, the substituents may be the same or different.

As used herein, a heterocydyl group is typically a non-aromatic, saturated or unsaturated $C_3$-$C_{10}$ carbocydic ring in which one or more, for example 1, 2, 3 or 4 of the carbon atoms are replaced by a heteroatom selected from N, O and S. Saturated heterocydyl groups are preferred. Examples of suitable heterocyclyl groups include piperidinyl, piperazinyl, morpholinyl, 4,5-dihydro-oxazolyl, 3-aza-tetrahydrofuranyl, imidazoildinyl and pyrrolidinyl groups. Where a heterocyclyl group carries 2 or more substituents, the substituents may be the same or different.

As used herein, a halogen atom, is typically a chlorine, fluorine or bromine atom.

As used herein, some of the atoms, groups, moieties, chains or cycles present in the general structures of the invention are "optionally substituted". This means that these atoms, groups, moieties, chains or cycles can be either unsubstituted or substituted by one or more, for example 1, 2, 3 or 4, substituents, whereby the hydrogen atoms bound to the unsubstituted atoms, groups, moieties, chains or cycles are replaced by chemically acceptable atoms, groups, moieties, chains or cycles. Typically when a cyclic group is bridged by an alkylene group, the bridging alkylene group is attached to the ring at non-adjacent atoms.

Compounds of the formula (I) containing one or more chiral centre may be used in enantiomerically or diastereoisomerically pure form, or in the form of a mixture of isomers.

As used herein, a pharmaceutically acceptable salt is a salt with a pharmaceutically acceptable acid or base. Pharmaceutically acceptable acids include both inorganic acids, for example hydrochloric, sulphuric, phosphoric, diphosphoric, hydrobromic and nitric acid and organic acids, for example citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, aralkyl amines and heterocyclic amines.

As used herein, an N-oxide is formed from the tertiary basic amines or pyridines present in the molecule, using a convenient oxidising agent.

Preferred compounds of the invention are those wherein $R^1$ and $R^2$ are independently an alkyl group optionally substituted by one or more, for example 1, 2, 3 or 4, substituents selected from hydroxy, halogen, alkoxy, alkylthio, amino, monoalkylamino, dialkylamino, hydroxycarbonyl, and alkoxycarbonyl groups; or a group of formula $-(CH_2)_n-R^6$, wherein n is an integer from 0 to 2 and $R^6$ represents a 3- to 7-membered aromatic or non-aromatic cyclic group having from 0 to 2 heteroatoms selected from nitrogen and oxygen. More preferred compounds are those wherein the alkyl chains, moieties or groups present $R^1$ and $R^2$ are $C_1$-$C_6$ alkyl chains, moieties or groups. Most preferably, $R^1$ and $R^2$ are both unsubstituted $C_1$-$C_6$ alkyl groups.

Further preferred compounds of the invention are those wherein $R^3$ represents hydrogen or a halogen atom, more preferably hydrogen or a chlorine atom, most preferably hydrogen.

Also preferred are compounds wherein $R^4$ is as defined above and $R^5$ is hydrogen, a group of formula $-(CH_2)_n-R^6$ or a hydrocarbon chain selected from alkyl, alkenyl and alkynyl, which is optionally substituted by one or more, for example 1, 2, 3 or 4, groups selected from $-(CH_2)_n-R^6$ and $-(CH_2)_n-O-R^6$; each $R^6$ being a phenyl or a pyridyl group, which is optionally substituted by one or more, for example 1, 2, 3 or 4, substituents selected from halogen, hydroxy, alkyl, alkoxy and alkylthio groups. More preferred compounds are those wherein $R^5$ is hydrogen, alkyl or benzyl. Most preferred compounds are those wherein $R^5$ is hydrogen or alkyl.

Typically, $R^4$ is:
hydrogen;
a group of formula $-(CH_2)_n-R^6$, wherein n is 0, 1 or 2 and $R^6$ is a 5- to 7-membered aromatic or non-aromatic cyclic group containing 0 to 2 heteroatoms selected from N, O and S, which is optionally substituted by one or more, for example 1, 2, 3 or 4, $R^7$ substituents selected from halogen, alkyl, alkenyl, alkynyl, aryl, arylalkyl, cycloalkyl, heteroaryl, heteroarylalkyl, heterocyclyl, hydroxy, alkylenedioxy, alkoxy, alkylthio, amino, monoalkylamino, dialkylamino, nitro, cyano, oxo, hydroxycarbonyl, alkoxycarbonyl, acylamino, carbamoyl, alkylcarbamoyl, dihydroxyphosphoryloxy and dialkoxyphosphoryloxy groups; the hydrocarbon chains and the cyclic moieties of these $R^7$ substituents being optionally substituted by one or more, for example 1, 2, 3 or 4, further $R^8$ substituents selected from halogen, hydroxy, oxo, cyano, alkya trifluoromethyl, alkoxy, alkylenedioxy, alkylthio, acylamino, carbamoyl, alkylcarbamoyl, dihydroxyphosphoryloxy, dialkoxyphosphoryloxy, hydroxyalkoxy, phenyl, alkoxycarbonyl, amino, monoalkylamino, dialkylamino and hydroxycarbonyl groups; or
an alkyl, alkenyl or alkynyl chain, which is optionally substituted by one or more, for example 1, 2, 3 or 4, substituents selected from $-(CH_2)_n-R^6$, $-O-(CH_2)_n-R^6$, $-S-(CH_2)_n-R^6$, $-NH-(CH_2)_n-R^6$, hydroxy, oxo, halogen, alkoxy, alkylthio, amino, monoalkylamino, and dialkylamino groups; the alkyl chains in the alkoxy, alkylthio, monoalkylamino and dialkylamino substituents being optionally substituted by one or more, for example 1, 2, 3 or 4, further substituents selected from $-(CH_2)_n-R^6$, hydroxy, oxo, halogen, alkoxy, alkylthio, amino, monoalkylamino and dialkylamino groups; and wherein each n is independently an integer from 0 to 4 and each $R^6$ is independenty a 5- or 6-membered aromatic or non-aromatic cyclic group having 0, 1 or 2 heteroatoms selected from N, O and S, and is optionally substituted by one or more, for example 1, 2, 3 or 4, $R^7$ substituents, wherein $R^7$ is as defined above and is optionally substituted by one or more, for example 1, 2, 3 or 4, further $R^8$ substituents, wherein $R^8$ is as defined above;

More preferably, $R^4$ is:
hydrogen;
a group of formula $-(CH_2)_n-R^6$ wherein n is 0, 1 or 2 and $R^6$ is a 5- to 6-membered heteroaryl or heterocyclyl group containing up to 2 heteroatoms selected from N, O and S, for example a piperidinyl, pyrrolidinyl or pyridyl group, which is optionally substituted by a $R^7$ substituent selected from halogen, alkyl, alkoxy, arylalkyl or heteroarylalkyl groups, the aryl and heteroaryl moieties of these arylalkyl and heteroarylalkyl $R^7$ substituents being optionally substituted by 1 or 2 further $R^8$ substituents selected from halogen, cyano, alkyl, trifluoromethyl, alkoxy and alkylenedioxy; or
an alkyl group which is optionally substituted by 1 or 2 substituents selected from amino monoalkylamino, dialkylamino, $-OR^6$ and $-SR^6$ substituents, wherein $R^6$ is a 5- or 6-membered heteroaryl group containing 1 or 2 heteroatoms, for example a pyridyl group, and is optionally substituted by one or more $R^7$ substituents selected from hydroxy, halogen, amino, monoalkylamino, dialkylamino, cyano, hydroxycarbonyl, alkoxycarbonyl, alkoxy, alkylenedioxy and alkylthio; and wherein the alkyl chains of each of the said monoalkylamino and dialkylamino substituents are optionally substituted by 1 or 2 further substituents selected from a hydroxy group and a group of formula $-(CH_2)_n-R^6$, wherein n is an integer from 0 to 4 and $R^6$ is an aryl group, for example a benzyl group.

Most preferably, $R^4$ is:
a group of formula $-(CH_2)_n-R^6$ wherein n is 0, 1 or 2 and $R^6$ is a 5- to 6-membered heteroaryl or heterocyclyl group containing up to 2 N atoms, for example a piperidinyl, pyrrolidinyl or pyridyl group, which is optionally substituted by a $R^7$ substituent selected from halogen, alkyl, alkoxy, arylalkyl or heteroarylalkyl groups, the aryl and heteroaryl moieties of these arylalkyl and heteroarylalkyl $R^7$ substituents being optionally substituted by 1 or 2 further $R^8$ substituents selected from halogen and alkoxy; or
an alkyl group which is optionally substituted by 1 or 2 substituents selected from monoalkylamino, dialkylamino, $-OR^6$ and $-SR^6$ substituents, wherein $R^6$ is a 5- or 6-membered heteroaryl group containing 1 or 2 N atoms, for example a pyridyl group, and is optionally substituted by one or more $R^7$ substituents selected from halogen and alkoxy; and wherein the alkyl chains of each of the said monoalkylamino and dialkylamino substituents are optionally substituted by 1 or 2 further substituents selected from a hydroxy group and a group of formula $-(CH_2)_n-R^6$, wherein n is an integer from 0 to 4 and $R^6$ is an aryl group, for example a benzyl group.

In other preferred embodiments of the invention $R^4$ and $R^5$ form, together with the nitrogen atom to which they are attached, an optionally bridged 5- to 7-membered aromatic or non-aromatic cyclic group which contains up to two nitrogen atoms, and which is optionally substituted by a group of formula —$(CH_2)_n$—$R^6$ or by a $R^7$ substituent selected from alkyl, alkenyl and alkynyl chains; the said alkyl, alkenyl and alkynyl chains being optionally substituted by one or more, for example 1, 2, 3 or 4, groups of formula —$(CH_2)_n$—$R^6$ or $R^8$ substituents selected from hydroxy, halogen, alkoxy, alkylthio, amino, monoalkylamino, and dialkylarmino groups; the alkyl chains in these $R^8$ substituents being optionally substituted by one or more, for example 1, 2, 3 or 4, further substituents selected from a group of formula —$(CH_2)_n$—$R^6$, and hydroxy, halogen, alkoxy, alkylthio, amino, monoalkylamino and dialkylamino groups; wherein each of the $R^6$ groups is optionallly substitued by one or more, for example 1, 2, 3 or 4, $R^7$ substituents and each of these $R^7$ substituents is optionally substituted by one or more, for example 1, 2, 3 or 4, $R^8$ substituents; each n, $R^6$, $R^7$ and $R^8$ being as defined above.

More preferably, $R^4$ and $R^5$ form, together with the N atom to which they are attached, a 5-, 6- or 7-membered saturated heterocyclic group which contains 1 or 2 nitrogen atoms and which optionally carries a bridging alkylene group (for example a piperazinyl, homopiperazinyl, or 2,5-methanopiperazinyl group), said cyclic group being optionally substituted by a group of formula —$(CH_2)_n$—$R^6$ wherein n is 0, 1 or 2 and $R^6$ is a 5- or 6-membered aromatic or non-aromatic ring containing 0, 1 or 2 heteroatoms selected from N, O and S (for example, a phenyl, furanyl, thienyl, pyridyl or pyrimidinyl ring), or by a $R^7$ substituent selected from alkyl and alkenyl groups, the group $R^6$ being optionally substituted by 1, 2 or 3 further substituents selected from haloalkyl, alkyl, alkoxy, alkylenedioxy, cyano and halogen groups, and the said $R^7$ substituent being optionally substituted by 1 or 2 phenyl substituents.

Particular individual compounds of the invention include:

6-[4-(4-Benzylpiperazine-1-sulphonyl)phenyl]-1,3-dimethyl-1,5-dihydropyrrolo[3,2-d]pyrimidine-2,4-dione 6-{4-[4-(4-Fluorobenzyl)piperazine-1-sulphonyl]phenyl}-1,3-dimethyl-1,5-dihydropyrrolo[3,2-d]pyrimidine-2,4-dione 6-{4-[4-(3-Fluorobenzyl)piperazine-1-sulphonyl]phenyl}-1,3-dimethyl-1,5-dihydropyrrolo[3,2-d]pyrimidine-2,4-dione 6-{4-[4-(2,4-Difluorobenzyl)piperazine-1-sulphonyl]phenyl}-1,3-dimethyl-1,5-dihydropyrrolo[3,2-d]pyrimidine-2,4-dione 6-{4-[4-(2-Fluorobenzyl)piperazine-1-sulphonyl]phenyl}-1,3-dimethyl-1,5-dihydropyrrolo[3,2-d]pyrimidine-2,4-dione 6-{4-[4-(4-Chlorobenzyl)piperazine-1-sulphonyl]phenyl}-1,3-dimethyl-1,5-dihydropyrrolo[3,2-d]pyrimidine-2,4-dione 6-{4-[4-(3-Chlorobenzyl)piperazine-1-sulphonyl]phenyl}-1,3-dimethyl-1,5-dihydropyrrolo[3,2-d]pyrimidine-2,4-dione 6-{4-[4-(4-Bromobenzyl)piperazine-1-sulphonyl]phenyl}-1,3-dimethyl-1,5-dihydropyrrolo[3,2-d]pyrimidine-2,4-dione 6-{4-[4-(2-Bromobenzyl)piperazine-1-sulphonyl]phenyl}-1,3-dimethyl-1,5-dihydropyrrolo[3,2-d]pyrimidine-2,4-dione 1,3-Dimethyl-6-{4-[4-(4-trifluoromethylbenzyl)piperazine-1-sulphonyl]phenyl}-1,5-dihydropyrrolo[3,2-d]pyrimidine-2,4-dione 6-{4-[4-(4-tert-Butylbenzyl)piperazine-1-sulphonyl]phenyl}-1,3-dimethyl-1,5-dihydropyrrolo[3,2-d]pyrimidine-2,4-dione 6-{4-[4-(4-Methoxybenzyl)piperazine-1-sulphonyl]phenyl}-1,3-dimethyl-1,5-dihydropyrrolo[3,2-d]pyrimidine-2,4-dione 6-{4-[4-(3-Methoxybenzyl)piperazine-1-sulphonyl]phenyl}-1,3-dimethyl-1,5-dihydropyrrolo[3,2-d]pyrimidine-2,4-dione 6-[4-(4-Benzo[1,3]dioxol-5-ylmethylpiperazine-1-sulphonyl)phenyl]-1,3-dimethyl-1,5-dihydro-pyrrolo[3,2-d]pyrimidine-2,4-dione 4-{4-[4-(1,3-Dimethyl-2,4-dioxo-2,3,4,5-tetrahydro-1H-pyrrolo[3,2-d]pyrimidin-6-yl)benzenesulphonyl]piperazin-1-ylmethyl}benzonitrile 6-[4-(4-Furan-3-ylmethylpiperazine-1-sulphonyl)phenyl]-1,3-dimethyl-1,5-dihydropyrrolo[3,2-d]pyrimidine-2,4-dione 1,3-Dimethyl-6-[4-(4-thiophen-2-ylmethylpiperazine-1-sulphonyl)phenyl]-1,5-dihydropyrrolo[3,2-d]pyrimidine-2,4-dione 6-{4-[4-(5-Chlorothiophen-2-ylmethyl)piperazine-1-sulphonyl]phenyl}-1,3-dimethyl-1,5-dihydropyrrolo[3,2-d]pyrimidine-2,4-dione 1,3-Dimethyl-6-[4-(4-pyridin-4-ylmethylpiperazine-1-sulphonyl)phenyl]-1,5-dihydropyrrolo[3,2-d]pyrimidine-2,4-dione 1,3-Dimethyl-6-{4-[4-(1-phenylethyl)piperazine-1-sulphonyl]phenyl}-1,5-dihydropyrrolo[3,2-d]pyrimidine-2,4-dione 6-[4-(4-Benzyl-[1,4]diazepane-1-sulphonyl)phenyl]-1,3-dimethyl-1,5-dihydropyrrolo[3,2-d]pyrimidine-2,4-dione 6-{4-[4-(4-Fluorobenzyl)[1,4]diazepane-1-sulphonyl]phenyl}-1,3-dimethyl-1,5-dihydropyrrolo[3,2-d]pyrimidine-2,4-dione 1,3-Dimethyl-6-{4-[4-((E)-3-phenylallyl)piperazine-1-sulphonyl]phenyl}-1,5-dihydropyrrolo[3,2-d]pyrimidine-2,4-dione 6-[4-((1S,4S)-5-Benzyl-2,5-diazabicyclo[2.2.1]heptane-2-sulphonyl)phenyl]-1,3-dimethyl-1,5-dihydropyrrolo[3,2-d]pyrimidine-2,4-dione 6-[4-(4-Benzhydrylpiperazine-1-sulphonyl)phenyl]-1,3-dimethyl-1,5-dihydropyrrolo[3,2-d]pyrimidine-2,4-dione N-[2-(Benzylmethylamino)ethyl]-4-(1,3-dimethyl-2,4-dioxo-2,3,4,5-tetrahydro-1H-pyrrolo[3,2-d]pyrimidin-6-yl)benzenesulphonamide 1,3-Dimethyl-6-[4-(4-pyridin-2-yl-piperazine-1-sulphonyl)phenyl]-1,5-dihydropyrrolo[3,2-d]pyrimidine-2,4-dione 6-{4-[4-(5-Methoxypyrimidin-4-yl)piperazine-1-sulphonyl]phenyl}-1,3-dimethyl-1,5-dihydropyrrolo[3,2-d]pyrimidine-2,4-dione N-(1-Benzylpiperidin-4-yl)-4-(1,3-dimethyl-2,4-dioxo-2,3,4,5-tetrahydro-1H-pyrrolo[3,2-d]pyrimidin-6-yl)benzenesulphonamide 4-(1,3-Dimethyl-2,4-dioxo-2,3,4,5-tetrahydro-1H-pyrrolo[3,2-d]pyrimidin-6-yl)-N-[1-(4-fluorobenzyl)piperidin-4-yl]benzenesulphonamide N-[1-(3,4-Dimethoxybenzyl)piperidin-4-yl]-4-(1,3-dimethyl-2,4-dioxo-2,3,4,5-tetrahydro-1H-pyrrolo[3,2-d]pyrimidin-6-yl)benzenesulphonamide 4-(1,3-Dimethyl-2,4-dioxo-2,3,4,5-tetrahydro-1H-pyrrolo[3,2-d]pyrimidin-6-yl)-N-(1-thiophen-2-ylmethylpiperidin-4-yl)benzenesulphonamide N-(1-Benzylpiperidin-4-yl)-4-(1,3-dimethyl-2,4-dioxo-2,3,4,5-tetrahydro-1H-pyrrolo[3,2-d]pyrimidin-6-yl)-N-methylbenzenesulphonamide N-(1-Benzylpyrrolidin-3-yl)-4-(1,3-dimethyl-2,4-dioxo-2,3,4,5-tetrahydro-1H-pyrrolo[3,2-d]pyrimidin-6-yl)benzenesulphonamide N-(1-Benzylpyrrolidin-3-yl)-4-(1,3-dimethyl-2,4-dioxo-2,3,4,5-tetrahydro-1H-pyrrolo[3,2-d]pyrimidin-6-yl)-N-methylbenzenesulphonamide 4-(1,3-Dimethyl-2,4dioxo-2,3,4,5-tetrahydro-1H-pyrrolo[3,2-d]pyrimidin-6-yl)-N-(6-methoxypyridin-3-yl)benzenesulphonamide 4-(1,3-Dimethyl-2,4-dioxo-2,3,4,5-tetrahydro-1H-pyrrolo[3,2-d]pyrimidin-6-yl)-N-(2-pyridin-2-ylethyl)benzenesulphonamide 4-(1,3-Dimethyl-2,4-dioxo-2,3,4,5-tetrahydro-1H-pyrrolo[3,2-d]pyrimidin-6-yl)-N-pyridin-2-ylbenzenesulphonamide 4-(1,3-Dimethyl-2,4-dioxo-2,3,4,5-tetrahydro-1H-pyrrolo[3,2-d]pyrimidin-6-yl)-N-(5-methylpyridin-2-yl)benzenesulphonamide 1,3-Dimethyl-6-[4-(4-phenylpiperazine-1-sulphonyl)phenyl]-1,5-dihydropyrrolo[3,2-d]pyrimidine-2,4-dione 1,3-Dimethyl-6-{4-[4-(4-trifluoromethylphenyl)piperazine-1-sulphonyl]-phenyl}-1,5-dihydropyrrolo[3,2-d]pyrimidine-2,4-dione 6-{4-[4-(3,5-Dichloropyridin-4-yl)piperazine-1-sulphonyl]phenyl}-1,3-dimethyl-1,5-dihydropyrrolo[3,2-d]pyrimidine-2,4-dione 6-[4-(4-Benzylpiperazine-1-sulphonyl)phenyl]-1,3-diethyl-1,5-dihydropyrrolo[3,2-d]pyrimidine-2,4-dione 1,3-Diethyl-6-{4-[4-(4-fluorobenzyl)piperazine-1-sulphonyl]phenyl}-1,5-dihydropyrrolo[3,2-d]pyrimidine-2,4-dione 1,3-Diethyl-6-{4-[4-(3-fluorobenzyl)piperazine-1-sulphonyl]phenyl}-1,5-dihydropyrrolo[3,2-d]pyrimidine-2,4-dione 6-{4-[4-(2,4-Difluorobenzyl)piperazine-1-sulphonyl]phenyl}-1,3-diethyl-1,5-dihydropyrrolo[3,2-d]pyrimidine-2,4-dione 6-{4-[4-(4-Chlorobenzyl)piperazine-1-sulphonyl]phenyl}-1,3-diethyl-1,5-dihydropyrrolo[3,2-d]pyrimidine-2,4-dione 6-{4-[4-(3-Chlorobenzyl)piperazine-1-sulphonyl]phenyl}-1,3-diethyl-1,5-dihydropyrrolo[3,2-d]pynimidine-2,4-dione 6-{4-[4-(4-Bromobenzyl)piperazine-1-sulphonyl]phenyl}-1,3-diethyl-1,5-dihydropyrrolo[3,2-d]pyrimidine-2,4-dione 6-{4-[4-(2-Bromobenzyl)piperazine-1-sulphonyl]phenyl}-1,3-diethyl-1,5-dihydropyrrolo[3,2-d]pyrimidine-2,4-dione 1,3-Diethyl-6-{4-[4-(4-trifluoromethylbenzyl)piperazine-1-sulphonyl]phenyl}-1,5-dihydropyrrolo[3,2-d]pyrimidine-2,4-dione 6-{4-[4-(4-tert-Butylbenzyl)piperazine-1-sulphonyl]phenyl}-1,3-diethyl-1,5-dihydropyrrolo[3,2-d]pyrimidine-2,4-dione 1,3-Diethyl-6-{4-[4-(4-methoxybenzyl)piperazine-1-sulphonyl]phenyl}-1,5-dihydropyrrolo[3,2-d]pyrimidine-2,4-dione 1,3-Diethyl-6-{4-[4-(3-methoxybenzyl)piperazine-1-sulphonyl]phenyl}-1,5-dihydropyrrolo[3,2-d]pyrimidine-2,4-dione 6-[4-(4-Benzo[1,3]dioxol-5-ylmethylpiperazine-1-sulphonyl)phenyl]-1,3-diethyl-1,5-dihydropyrrolo[3,2-d]pyrimidine-2,4-dione 4-{4-[4-(1,3-Diethyl-2,4-dioxo-2,3,4,5-tetrahydro-1H-pyrrolo[3,2-d]pyrimidin-6-yl)benzenesulphonyl]piperazin-1-ylmethyl}benzonitrile 1,3Diethyl-6-[4-(4-furan-2-ylmethylpiperazine1-sulphonyl)phenyl]-1,5-dihydropyrrolo[3,2-d]pyrimidine-2,4-dione 1,3Diethyl-6-[4-(4thiophen-2-ylmethylpiperazine-1-sulphonyl)phenyl]-1,5-dihydropyrrolo[3,2-d]pyrimidine-2,4-dione 6-{4-[4-(5-Chlorothiophen-2-ylmethyl)piparazine-1-sulphonyl]phenyl}-1,3-diethyl-1,5-dihydropyrrolo[3,2-d]pyrimidine-2,4dione 1,3-Diethyl-6-[4-(4-pyridinyl-4-methylpiperazine-1-sulphonyl)phenyl]-1,5-dihydropyrrolo[3,2-d]pyrimidine-2,4-dione 1,3-Diethyl-6-{4-[4-(1-phenylethyl)piperazine-1-sulphonyl]phenyl}-1,5-dihydropyrrolo[3,2-d]pyrimidine-2,4-dione 1,3Diethyl-6-{4-[4-(4-fluorobenzyl-[1,4]diazepane1-sulphonyl]phenyl}-1,5-dihydropyrrolo[3,2-d]pyrimidine-2,4-dione 1,3-Diethyl-6-[4-(4-phenethylpiperazine-1-sulphonyl)phenyl]-1,5dihydropyrrolo[3,2-d]pyrimidine-2,4dione 6-[4-((1S,4S)-5-Benzyl-2,5-diazabicyclo[2.2.1]heptane-2-sulphonyl)phenyl]-1,3-diethyl-1,5-dihydropyrrolo[3,2-d]pyrimidine-2,4-dione N-[2-(Benzylmethylamino)ethyl]-4-(diethyldioxo-2,3,4,5-tetrahydro-1H-pyrrolo[3,2-d]pyrimidin-6-yl)benzenesulphonamide N-{2-[Benzyl-(2-hydroxyethyl)amino]ethyl}-4-(diethyldioxo-2,3,4,5-tetrahydro-1H-pyrrolo[3,2-d]pyrimiding-6-yl)benzenesulphonamide 1,3-Diethyl-6-[4-(4-pyridin-2-ylpiperazine-1-sulphonyl)phenyl]-1,5dihydropyrrolo[3,2-d]pyrimidine-2,4dione N-(1-Benzylpiperidin-4-yl)-4-(1,3-diethyl-2,4-dioxo-2,3,4,5-tetrahydro-1H-pyrrolo[3,2-d]pyrimidin-6-yl)benzenesulphonamide 4-(1,3-Diethyl-2,4-dioxo-2,3,4,5-tetrahydro-1H-pyrrolo[3,2-d]pyrimidin-6-yl)-N-[1-(4-fluorobenzyl)piperidin-4yl]benzenesulphonamide 4-(1,3-Diethyl-2,4-dioxo-2,3,4,5-tetrahydro-1H-pyrrolo[3,2-d]pyrimidin-6-yl)-N-[1-(3,4-dimethoxybenzyl)piperidin-4-yl]benzenesulphonamide 4-(1,3-Diethyl-2,4-dioxo-2,3,4,5-tetrahydro-1H-pyrrolo[3,2-d]pyrimidin-6-yl)-N-(1-thiophen-2-ylmethylpiperidin-4-yl)benzenesulphonamide N-(1-Benzylpiperidin-4yl)-4-(1,3-diethyl-2,4-dioxo-2,3,4,5-tetrahydro-1H-pyrrolo[3,2-d]pyrimidin-6-yl)-N-methylbenzenesulphonamide N-(1-Benzylpyrrolidin-3-yl)-4-(1,3-diethyl-2,4-dioxo-2,3,4,5-tetrahydro-1H-pyrrolo[3,2-d]pyrimidin-6-yl)benzenesulphonamide N-(1-Benzylpyrrolidin-3-yl)-4-(1,3diethyl-2,4-dioxo-2,3,4,5-tetrahydro-1H-pyrrolo[3,2-d]pydimidin-6-yl)-N-methylbenzenesulphonamide 4-(1,3-Diethyl-2,4-dioxo-2,3,4,5-tetrahydro-1H-pyrrolo[3,2-d]pyrimidin-6-yl)-N-(2-pyridin-2-yl-ethyl)benzenesulphonamide 6-[4-(4-Benzylpiperazine-1-sulphonyl)phenyl]-1,3-dipropyl-1,5-dihydro-pyrrolo[3,2-d]pyrimidine-2,4-dione 6-{4-[4-(4-Fluorobenzyl)piperazine-1-sulphonyl]phenyl}-1,3-dipropyl-1,5-dihydropyrrolo[3,2-d]pyrimidine-2,4-dione 6-{4-[4-(3-Fluorobenzyl)piperazine-1-sulphonyl]phenyl}1,3-dipropyl-1,5-dihydropyrrolo[3,2-d]pydimidine-2,4-dione 6-{4-[4-(2,4-Difluorobenzyl)piperazine-1-sulphonyl]phenyl}-1,3dipropyl-1,5-dihydropyrrolo[3,2-d]pydimidine-2,4-dione 6-{4-[4-(4-Chlorobenzyl)piperazine-1-sulphonyl]phenyl}-1,3-dipropyl-1,5-dihydropyrrolo[3,2-d]pyrimidine-2,4-dione 6-{4-[4-(3-Chlorobenzyl)piperazine-1-sulphonyl]phenyl}1,3-dipropyl-1,5-dihydropyrrolo[3,2-d]pyrimidine-2,4-dione 6-{4-[4-(4-Bromobenzyl)piperazine-1-sulphonyl]phenyl}-1,3-dipropyl-1,5-dihydropyrrolo[3,2-d]pyrimidine-2,4-dione 6-{4-[4-(2-Bromobenzyl)piperazine-1-sulphonyl]phenyl}-1,3-dipropyl-1,5-dihydropyrrolo[3,2-d]pyrimidine-2,4-dione 1,3-Dipropyl-6-{4-[4-(4-trifluoromethylbenzyl)piperazine-1-sulphonyl]phenyl}-1,5-dihydropyrrolo[3,2-d]pydimidine-2,4-dione 6-{4-[4-(4-tert-Butylbenzyl)piperazine-1-sulphonyl]phenyl}-1,3-dipropyl-1,5-dihydropyrrolo[3,2-d]pyrimidine-2,4-dione 6-{4-[4-(4-Methoxybenzyl)piperazine-1-sulphonyl]phenyl}-1,3-dipropyl-1,5-dihydropyrrolo[3,2-d]pyrimidine-2,4-dione 6-{4-[4-(3-Methoxybenzyl)piperazine-1-sulphonyl]phenyl}-1,3-dipropyl-1,5-dihydropyrrolo[3,2-d]pyrimidine-2,4-dione 6-[4-(4-Benzo[1,3]dioxol-5-ylmethylpiperazine-1-sulphonyl)phenyl]-1,3-dipropyl-1,5-dihydropyrrolo[3,2-d]pyrimidine-2,4-dione 4-{4-[4-(2,4-Dioxo-1,3dipropyl-2,3,4,5-tetrahydro-1H-pyrrolo[3,2-d]pyrimidin-6-yl)benzenesulphonyl]piperazin-1-ylmethyl}benzonitrile 1,3-Dipropyl-6-[4-(4-thiophen-2-ylmethylpiperazine-1-sulphonyl)phenyl]-1,5-dihydropyrrolo[3,2-d]pyrimidine-2,4-dione 6{4-[4-(5-Chlorothiophen-2-ylmethyl)piperazine-1-sulphonyl]phenyl}-1,3-dipropyl-1,5-dihydropyrrolo[3,2-d]pyrimidine-2,4-dione 1,3-Dipropyl-6-[4-(4-pyridin-4-ylmethylpiperazine-1-sulphonyl)phenyl]-1,5-dihydropyrrolo[3,2-d]pyrimidine-2,4-dione 6-{4-[4-(1-Phenylethyl)piperazine-1-sulphonyl]phenyl}-1,3-dipropyl-1,5-dihydropyrrolo[3,2-d]pyrimidine-2,4-dione 6-{4-[4-(4-Fluorobenzyly[1,4]diazepane-1-sulphonyl]phenyl}-1,3-dipropyl-1,5-dihydropyrrolo[3,2-d]pyrimidine-2,4-dione 6-[4-(4-Phenethylpiperazine-1-sulphonyl)phenyl]-1,3-dipropyl-1,5-dihydropyrrolo[3,2-d]pyrimidine-2,4-dione 1,3-Dipropyl-6-[4-(4-pyridin-2-ylpiperazine-1-sulphonyl)pheny]-1,5-dihydropyrrolo[3,2-d]pyrimidine-2,4-dione N-(1-Benzylperidin-4-yl)-4-(2,4-dioxo-1,3-dipropyl-2,3,4,5-tetrahydro-1H-pyrrolo[3,2-d]pyrimidin-6-yl)benzenesulphonamide 4-(2,4-Dioxo-1,3-dipropyl-2,3,4,5-tetrahydro-1H-pyrrolo[3,2-d]pyrimidin-6-yl)-N-[1-(4-fluorobenzylpiperidin-4-yl]benzenesulphonamide N-[1-(3,4-Dimethoxybenzyl)piperidin-4-yl]-4-(2,4-dioxo-1,3-dipropyl-2,3,4,5-tetrahydro-1H-pyrrolo[3,2-d]pyrimidin-6-yl)benzenesulphonamide 4-(2,4-Dioxo-1,3-dipropyl-2,3,4,5-tetrahydro-1H-pyrrolo[3,2-d]pyrimidin-6-yl)-N-(1-thiophen-2-yl-methylpiperidin-4-yl)benzenesulphonamide N-(1-Benzylpiperidin-4-yl)-4-(2,4-dioxo-1,3-dipropyl-2,3,4,5-tetrahydro-1H-pyrrolo[3,2-d]pyrimidin-6-yl)-N-methylbenzenesulphonamide N-(1-Benzylpyrrolidin-3-yl)-4-(2,4-dioxo-1,3-dipropyl-2,3,4,5-tetrahydro-1H-pyrrolo[3,2-d]pyrimidin-6-yl)benzenesulphonamide 4-(2,4-Dioxo-1,3-dipropyl-2,3,4,5-tetrahydro-1H-pyrrolo[3,2-d]pyrimidin-6-yl)-N-(6-methoxypyridin-3-yl)benzenesulphonamide 4-(2,4-Dioxo-1,3-dipropyl-2,3,4,5-tetrahydro-1H-pyrrolo[3,2-d]pyrimidin-6-yl)-N-(2-pyridin-2-yl-ethyl)benzenesulphonamide 4-(2,4Dioxo-1,3-dipropyl-2,3,4,5-tetrahydro-1H-pyrrolo[3,2-d]pyrimidin-6-yl)-N-pyridin-2-ylbenzenesulphonamide 6-[4-(4-Benzylpiperazine-1-sulphonyl)phenyl]-1-methyl-3-propyl-1,5-dihydropyrrolo[3,2-d]pyrimidine-2,4-dione 6-{4-[4-(4-Fluorobenzyl)piperazine-1-sulphonyl]phenyl}-1-methyl-3-propyl-1,5-dihydropyrrolo[3,2-d]pyrimidine-2,4-dione 6-{4-[4-(3Fluorobenzyl)piperazine-1-sulphonyl]phenyl}-1-methyl-3propyl-1,5-dihydropyrrolo[3,2-d]pyrimidine-2,4-dione 6-{4-[4-(2,4-Difluorobenzyl)piperazine-1-sulphonyl]phenyl}-1-methyl-3-propyl-1,5-dihydropyrrolo[3,2-d]pyrimidine-2,4-dione 6-{4-[4-(4-Chlorobenzyl)piperazine-1-sulphonyl]phenyl}-1-methyl-3-propyl1,5-dihydropyrrolo[3,2-d]pyrimidine-2,4-dione 6-{4-[4-(3-Chlorobenzyl)piperazine-1-sulphonyl]phenyl}-1-methyl-3-propyl-1,5-dihydropyrrolo[3,2-d]pyrimidine-2,4-dione 6-{4-[4-(4-Bromobenzyl)piperazine-1-sulphonyl]phenyl}-1-methyl-3-propyl-1,5-dihydropyrrolo[3,2-d]pyrimidine-2,4-dione 6-{4-[4-(2-Bromobenzyl)piperazine-1-sulphonyl]phenyl}-1-methyl-3propyl-1,5-dihydropyrrolo[3,2-d]pyrimidine-2,4-dione 1-Methyl-3propyl-6-{4-[4-(4-trifluoromethylbenzyl)piperazine-1-sulphonyl]phenyl}-1,5-dihydropyrrolo[3,2-d]pyrimidine-2,4-dione 6-{4-[4-(4-tert-Butylbenzyl)piperazine-1-sulphonyl]phenyl}-1-methyl-3-propyl-1,5-dihydropyrrolo[3,2-d]pyrimidine-2,4-dione 6-{4-[4-(4-Methoxybenzyl)piperazine-1-sulphonyl]phenyl}-1-methyl-3-propyl-1,5-dihydropyrrolo[3,2-d]pyrimidine-2,4-dione 6-{4-[4-(3-Methoxybenzyl)piparazine-1-sulphonyl]phenyl}-1-methyl-3-propyl-1,5-dihydropyrrolo[3,2-d]pyrimidine-2,4-dione 6[4-(4-Benzol[1,3]dioxol-5-ylmethylpiperazine-1-sulphonyl)phenyl]-1-methyl-3-propyl-1,5-dihydropyrrolo[3,2-d]pyrimidine-2,4-dione 4-{4-[4-(1-Methyl-2,4-dioxo-3-propyl-2,3,4,5-tetrahydro-1H-pyrrolo[3,2-d]pyrimidin-6-yl)benzenesulphonyl]piperazin-1-ylmethyl}benzonitrile 6-[4-(4-Furan-3-ylmethylpiperazine-1-sulphonyl)phenyl]-1-methyl-3-propyl-1,5-dihydropyrrolo[3,2-d]pyrimidine-2,4-dione 1-Methyl-3-propyl-6-[4-(4-thiophen-2-ylmethylpiperazine-1-sulphonyl)phenyl]-1,5-dihydropyrrolo[3,2-d]pyrimidine-2,4-dione 6-{4-[4-(5-Chlorothiophen-2-ylmethyl)piperazine-1-sulphonyl]phenyl}-1-methyl-3-propyl-1,5-dihydropyrrolo[3,2-d]pyrimidine-2,4-dione 1-Methyl-3-propyl-6-[4-(4-pyridin-4-ylmethylpiperazine-1-sulphonyl)phenyl]-1,5-dihydropyrrolo[3,2-d]pyrimidine-2,4-dione 6{4-[4-(4-Fluorobenzyl)-[1,4]diazepane-1-sulphonyl]phenyl}-1-methyl-3-propyl-1,5-dihydropyrrolo[3,2-d]pyrimidine-2,4-dione N-[2-(Benzylmethylamino)ethyl]-4-(methyldioxopropyl-2,3,4,5-tetrahydro-1H-pyrrolo[3,2-d]pyrimidin-6-yl)benzenesulphonamide 1-Methyl-3-propyl-6-[4-(4-pyridin-2-yipiperazine-1-sulphonyl)phenyl]-1,5-dihydropyrrolo[3,2-d]pyrimidin-2,4-dione N-(1-Benzylpiperidin-4-yl)-4-(1-methy-2,4-dioxo-3-propyl-2,3,4,5-tetrahydro-1H-pyrrolo[3,2-d]pyrimidin-6-yl)benzenesulphonamide N-[1-(4-Fluoro-benzyl)piperidin-4-yl]-4-(1-methyl-2,4-dioxo-3-propyl-2,3,4,5-tetrahydro-1H-pyrrolo[3,2-d]pyrimidin-6-yl)benzenesulphonamide N-[1-3,4Dimethoxybenzyl)piperidin-4-yl]-4-(1-methyl-2,4-dioxo-3-propyl-2,3,4,5-tetrahydro-1H-pyrrolo[3,2-d]pyrimidin-6-yl)benzenesulphonamide 4-(1-Methyl-2,4-dioxo-3-propyl-2,3,4,5-tetrahydro-1H-pyrrolo[3,2-d]pyrimidin-6-yl)-N-(1-thiophen-2-ylmethylpiperidin-4-yl)benzenesulphonamide N-(1-Benzylpiperdin-4-yl)-N-methyl-4-(1-methyl-2,4-dioxo-3-propyl-2,3,4,5-tetrahydro-1H-pyrrolo[3,2-d]pyrimidin-6-yl)benzenesulphonamide 4-(1-Methyl-2,4-dioxo-3-propyl-2,3,4,5-tetrahydro-1H-pyrrolo[3,2-d]pyrimidin-6-yl)-N-(2-pyridin-2-ylethyl)benzenesulphonamide 6-[4-(4-Benzylpiperazine-1-sulphonyl)phenyl]-3-methyl-1-propyl-1,5-dihydropyrrolo[3,2-d]pyrimidine-2,4-dione 6-{4-[4-(4-Fluorobenzyl)piperazin-1-sulphonyl]phenyl}-3-methyl-1-propyl-1,5-dihydropyrrolo[3,2-d]pyrimidine-2,4-dione 6-{4-[4-(3-Fluorobenzyl)piperazin-1-sulphonyl]phenyl}-3-methyl-1-propyl-1,5-dihydropyrrolo[3,2-d]pyrimidine-2,4-dione 6-{4-[4-(4-Chlorobenzyl)piperazin-1-sulphonyl]phenyl}-3-methyl-1-propyl-1,5-dihydropyrrolo[3,2-d]pyrimidine-2,4-dione 6-{4-[4-(3-Chlorobenzyl)piperazin-1-sulphonyl]phenyl}-3-methyl-1-propyl-1,5-dihydropyrrolo[3,2-d]pyrimidine-2,4-dione 6-{4-[4-(4-Bromobenzyl)piperazin-1-sulphonyl]phenyl}-3-methyl-1-propyl-1,5-dihydropyrrolo[3,2-d]pyrimidine-2,4-dione 6-{4-[4-(2-Bromobenzyl)piperazin-1-sulphonyl]phenyl}-3-methyl-1-propyl-1,5-dihydropyrrolo[3,2-d]pyrimidine-2,4-dione 3-Methyl-1-propyl-6-{4-[4-(4-trifluoromethylbenzyl)piperazine-1-sulphonyl]phenyl}-1,5-dihydropyrrolo[3,2-d]pyrimidine-2,4-dione 6-{4-[4-(4-tert-Butylbenzyl)piperazine-1-sulphonyl]phenyl}-3-methyl-1-propyl-1,5-dihydropyrrolo[3,2-d]pyrimidine-2,4-dione 6-{4-[4-(4-Methoxybenzyl)piperazine-1-sulphonyl]phenyl}-3methyl-1-propyl-1,5-dihydropyrrolo[3,2-d]pyrimidine-2,4-dione 6-{4-[4-(3-Methoxybenzyl)piperazine-1-sulphonyl]phenyl}-methyl-1-propyl-1,5-dihydropyrrolo[3,2-d]pyrimidine-2,4-dione 6-[4-(4-Benzol[1,3]dioxol-5-ylmethylpiperazine-1-sulphonyl)phenyl]-3-methyl-1-propyl-1,5-dihydropyrrolo[3,2-d]pyrimidine-2,4-dione 4-{4-[4-(3-Methyl-2,4-dioxo-1-propyl-2,3,4,5-tetrahydro-1H-pyrrolo[3,2-d]pyrimidin-6-yl)benzenesulphonyl]piperazin-1-ylmethyl}benzonitrile 3-Methyl-1-propyl-6-[4-(4-thiophen-2-ylmethylpiperazine-1-sulphonyl)phenyl]-1,5-dihydropyrrolo[3,2-d]pyrimidine-2,4-dione 6-{4-[4-(5-Chlorothiophen-2-ylmethyl)piperazine-1-sulphonyl]-phenyl}-3-methyl-1-propyl-1,5-dihydropyrrolo[3,2-d]pyrimidine-2,4-dione 3-Methyl-1-propyl-6-[4-(4-pyridin-4-ylmethylpiperazine-1-sulphonyl)phenyl]-1,5-dihydropyrrolo[3,2-d]pyrimidine-2,4-dione 3-Methyl-6-{4-[4-(1-phenylethyl)piperazine-1-sulphonyl]-phenyl}-1-propyl-1,5-dihydropyrrolo[3,2-d]pyrimidine-2.4-dione 6-[4-(4-Benzyl[1,4]diazepane-1-sulphonyl)phenyl]-3-methyl-1-propyl-1,5-dihydropyrrolo[3,2-d]pyrimidine-2,4-dione 6-{4-[4-(4-Fluorobenzyl)[1,4]diazepane-1-sulphonyl]-phenyl}-methyl-1-propyl-1,5-dihydropyrrolo[3.2-d]pyrimidine-2,4-dione 3-Methyl-6-[4-(4-phenethylpiperazine-1-sulphonyl)phenyl]-1-propyl-1,5-dihydropyrrolo[3,2-d]pyrimidine-2.4-dione 6-[4-(5-Benzyl-2,5-diazablcyclo[2.2.1]heptane-2-sulphonyl)-phenyl]-3-methyl-1-propyl-1,5-dihydropyrrolo[3,2-d]pyrimidine-2,4-dione N-[2-(Benzylmethylamino)ethyl]-4-(3-methyl-2,4-dioxo-1-propyl-2,3,4,5-tetrahydro-1H-pyrrolo[3,2-d]pyrimidin-6-yl)benzenesulphonamide N-{2-[Benzyl-(2-hydroxyethyl)amino]ethyl}-4-(3-methyl-2,4-dioxo-1-propyl-2,3,4,5-tetrahydro-1H-pyrrolo[3,2-d]pyrimidin-6-yl)benzenesulphonamide 3-Methyl-1-propyl-6-[4-(4-pyridin-2-yl-piperazine-1-sulphonyl)phenyl]-1,5-dihydropyrrolo[3,2-d]pyrimidine-2,4-dione N-(1-Benzylpiperidin-4-yl)-4-(3-methyl-2,4-dioxo-1-propyl-2,3,4,5-tetrahydro-1H-pyrrolo[3.2-d]pyrimidin-6-yl)benzenesulphonamide N-[1-(4-Fuorobenzyl)-piparidin-4-yl]-4-(3-methyl-2,4-dioxo-1-propyl-2.3,4,5-tstrahydro-1H-pyrrolo[3,2-d]pyrimidin-6-yl)benzenesulphonamide N-[1-(3,4-Dimethoxybenzyl)piperidin-4-yl]-4-(3-methyl-2,4-dioxo-1-propyl-2,3,4,5-tetrahydro-1H-pyrrolo[3,2-d]pyrimidin-6-yl)benzenesulphonamide 4-(3-Methyl-2,4-dioxo-1-propyl-2,3,4,5-tetrahydro-1H-pyrrolo[3,2-d]pyrimidin-6-yl)-N-(1-thiophen-2-ylmethylpiperidin-4-yl)benzenesulphonamide N-(1-Benzylpiperidin-4-yl)-N-methyl-4-(3-methyl-2,4-dioxo-1-propyl-2,3,4,5-tetrahydro-1H-pyrrolo[3,2-d]pyrimidin-6-yl)benzenesulphonamide 4-(3-Methyl-2,4-dioxo-1-propyl-2,3,4,5-tetrahydro-1H-pyrrolo[3,2-d]pyrimidin-6-yl)-N-(2-pyridin-2-yl-ethyl)benzenesulphonamide 6-[4-(4-Benzylpiperazine-1-sulphonyl)phenyl]-7-chloro-1,3-dimethyl-1,5-dihydropyrrolo[3,2-d]pyrimidine-2,4-dione 4-(1,3-Dimethyl-2,4-dioxo-2,3,4,5-tetrahydro-1H-pyrrolo[3,2-d]pyrimidin-6yl)-N-pyridin-2-ylmethylbenzenesulfonamide 4-(1,3-Dimethyl-2,4-dioxo-2,3,4,5-tetrahydro-1H-pyrrolo[3,2-d]pyrimidin-6-yl)-N-pyridin-3-ylmethylbenzenesulfonamide 4-(1,3-Dimethyl-2,4-dioxo-2,3,4,5-tetrahydro-1H-pyrrolo[3,2-d]pyrimidin-6-yl)-N-pyridin-4-ylmethylbenzenesulfonamide 4-(1,3-Dimethyl-2,4-dioxo-2,3,4,5-tetrahydro-1H-pyrrolo[3,2-d]pyrimidin-6-yl)-N-(6-methoxypyridin-3-ylmethyl)benzenesulfonamide N-(3-Chloropyridin-4-ylmethyl)-4-(1,3-dimethyl-2,4-dioxo-2 3,4,5-tetrahydro-1H-pyrrolo[3,2-d]pyrimidin-6-yl)benzenesulfonamide 4-(1,3-Dimethyl-2,4-dioxo-2,3,4,5-tetrahydro-1H-pyrrolo[3,2-d]pyrimidin-6-yl)-N-methyl-N-(2-pyridin-2-ylethyl)benzenesulfonamide 4-(1,3-Dimethyl-2,4-dioxo-2,3,4,5-tetrahydro-1H-pyrrolo[3,2-d]pyrimidin-6-yl)-N-(2-pyridin-3-ylethyl)benzenesulfonamide 4-(1,3-Dimethyl-2,4-dioxo-2,3,4,5-tetrahydro-1H-pyrrolo[3,2-d]pyrimidin-6-yl)-N-(2-pyridin-4-ylethyl)benzenesulfonamide 4-(1,3-Dimethyl-2,4-dioxo-2,3,4,5-tetrahydro-1H-pyrrolo[3,2-d]pyrimidin-6-yl)-N-[2-(pyridin-2-yloxy)ethyl]benzenesulfonamide 4-(1,3-Dimethyl-2,4-dioxo-2,3,4,5-tetrahydro-1H-pyrrolo[3,2-d]pyrimidin-6-yl)-N-[2-(6-methoxypyridin-2-yloxy)ethyl]benzenesulfonamide 4-(1,3-Dimethyl-2,4-dioxo-2,3,4,5-tetrahydro-1H-pyrrolo[3,2-d]pyrimidin-6-yl)-N-[2-(4-methylpyridin-2-yloxy)ethyl]benzenesulfonamide N-[2-(5-Chloropyridin-2-yloxy)ethyl]-4-(1,3-dimethyl-2,4-dioxo-2,3,4,5-tetrahydro-1H-pyrrolo[3,2-d]pyrimidin-6-yl)benzenesulfonamide 4-(1,3-Dimethyl-2,4-dioxo-2,3,4,5-tetrahydro-1H-pyrrolo[3,2-d]pyrimidin-6-yl)-N-[2-(5-trifiuoromethylpyridin-2-yloxy)ethyl]benzenesulfonamide 4-(1,3-Dimethyl-2,4-dioxo-2,3,4,5-tetrahydro-1H-pyrrolo[3,2-d]pyrimidin-6-yl)-N-[2-(pyridin-3-yloxy)ethyl]benzenesulfonamide 4-(1,3-Dimethyl-2,4-dioxo-2,3,4,5-tetrahydro-1H-pyrrolo[3,2-d]pyrimidin-6-yl)-N-[2-(pyrazin-2-yloxy)ethyl]benzenesulfonamide 4-(1,3-Dimethyl-2,4-dioxo-2,3,4,5-tetrahydro-1H-pyrrolo[3,2-d]pyrimidin-6-yl)-N-[2-(pyridin-2-ylsulfanyl)ethyl]benzenesulfonamide 4-(1,3-Dimethyl-2,4-dioxo-2,3,4,5-tetrahydro-1H-pyrrolo[3,2-d]pyrimidin-6-yl)-N-[2-(pyrimidin-2-ylsulfanyl)ethyl]benzenesulfonamide N-Benzyl-4-(1,3-dimethyl-2,4-dioxo-2,3,4,5-tetrahydro-1H-pyrrolo[3,2-d]pyrimidin-6-yl)-N-[2-(pyridin-2-yloxy)ethyl]benzenesulfonamide N-Benzyl-4-(1,3-dimethy-2,4-dioxo-2,3,4,5-tetrahydro-1H-pyrrolo[3,2-d]pyrimidin-6yl)-N-[2-(6-methoxypyridin-2-yloxy)ethyl]benzenesulfonamide N-Benzyl-N-[2-(6-chloropyridin-3-yloxy)ethyl]-4-(1,3-dimethyl-2,4-dioxo-2,3,4,5-tetrahydro-1H-pyrrolo[3,2-d]pyrimidin-6-yl)benzenesulfonarnide 6-[4-(4-Benzylpiperidine-1-sulfonyl)phenyl]-1,3-dimethyl-1,5-dihydropyrrolo[3,2-d]pyrimidine-2,4-dione 6-{4-[4-(3-Methoxyphenyl)piperidine-1-sulfony]phenyi}-3-dimethyl-1,5-dihydropyrrolo[3,2-d]pyrimidine-2,4-dione 4-(1,3-Diethyl-2,4-dioxo-2,3,4,5-tetrahydro-1H-pyrrolo[3,2-d]pyrimidin-6-yl)-N-pyridin-2-ylmethylbenzenesulfonamide 4-(1,3-Diethyl-2,4-dioxo-2,3,4,5-tetrahydro-1H-pyrrolo[3,2-d]pyrimidin-6-yl)-N-pyridin-3-ylmethylbenzenesulfonamide 4-(1,3-Diethyl-2,4-dioxo-2,3,4,5-tetrahydro-1H-pyrrolo[3,2-d]pyrimidin-6-yl)-N-pyridin-4-ylmethylbenzenesulfonamide 4-(1,3-Diethyl-2,4-dioxo-2,3,4,5-tetrahydro-1H-pyrrolo[3,2-d]pyrimidin-6-yl)-N-(6-methoxypyridin-3-ylmethyl)benzenesulfonamide 4-(1,3-Diethyl-2,4-dioxo-2,3,4,5-tetrahydro1H-pyrrolo[3,2-d]pyrimidin-6-yl)-N-methyl-N-(2-pyridin-2-ylethyl)benzenesulfonamide 4-(1,3-Diethyl-2,4-dioxo-2,3,4,5-tetrahydro-1H-pyrroio[3,2-d]pyrimidin-6-yl)-N-(2-pyridin-3-ylethyl)benzenesulfonamide 4-(1,3-Diethyl-2,4-dioxo-2,3,4,5-tetrahydro-1H-pyrrolo[3,2-d]pyrimidin-6-yl)-N-(2-pyridin-4-ylethyl)benzenesulfonamide 4-(1,3-Diethyl-2,4-dioxo-2,3,4,5-tetrahydro-1H-pyrrolo[3,2-d]pyrimidin-6-yl)-N-[2-(pyridin-3-yloxy)ethyl]benzenesulfonamide N-Benzyl4-(1,3-diethyl-2,4-dioxo-2,3,4,5-tetrahydro-1H-pyrrolo[3,2-d]pyrimidin-6-yl)-N-[2-(pyridin-2-yloxy)ethyl]benzenesuffonamide 4-(2,4-Dioxo-1,3dipropyl-2,3,4,5-tetrahydro-1H-pyrrolo[3,2-d]pyrimidin-6-yl)-N-methyl-N-(2-pyridin-2-yl-ethyl)benzenesulfonamide 4-(1-Methyl-2,4-dioxo-3-propyl-2,3,4,5-tetrahydro-1H-pyrrolo[3,2-d]pyrimidin-6-yl)-N-pyridin-2-ylmethylbenzenesulfonamide 4-(1-Methyl-2,4-dioxo-3-propyl-2,3,4,5-tetrahydro-1H-pyrrolo[3,2-d]pyrimidin-6-yl)-N-pyridin-3-ylmethylbenzenesulfonamide N-(6-Methoxypyridin-3-ylmethyl)-4-(1-methyl-2,4-dioxo-3-propyl-2,3,4,5-tetrahydro-1H-pyrrolo[3,2-d]pyrimidin-6-yl)benzenesulfonamide N-Methyl-4-(1-methyl-2,4-dioxo-3-propyl-2,3,4,5-tetrahydro-1H-pyrrolo[3,2-d]pyrimidin-6-yl)-N-(2-pyridin-2-ylethyl)benzenesulfonamide 4-(1-Methyl-2,4-dioxo-3-propyl-2,3,4,5-tetrahydro-1H-pyrrolo[3,2-d]pyrimidin-6-yl)-N-(2-pyridin-3-ylethyl)benzenesulfonamide 4-(1-Methyl-2,4-dioxo-3-propyl-2,3,4,5-tetrahydro-1H-pyrrolo[3,2-d]pyrimidin-6-yl)-N-(2-pyridin-4-ylethyl)benzenesulfonamide 4-(1-Methyl-2,4-dioxo-3-propyl-2,3,4,5-tetrahydro-1H-pyrrolo[3,2-d]pyrimidin-6-yl)-N-[2-(pyridin-2-yloxy)ethyl]benzenesulfonamide N-Benzyl-4-(1-methyl-2,4-dioxo-3-propyl-2,3,4,5-tetrahydro-1H-pyrrolo[3,2d]pyrimidin-6-yl)-N-[2-(pyridin-2-yloxy)ethyl]benzenesulfonamide 4-(3-Methyl-2,4-dioxo-1-propyl-2,3,4,5-tetrahydro 1H-pyrrolo[3,2-d]pyrimidin-6-yl)-N-pyridin-2-ylmethylbenzenesulfonamide 4-(3-Methyl-2,4-dioxo-1-propyl-2,3,4,5-tetrahydro1H-pyrrolo[3,2-d]pyrimidin-6-yl)-N-pyridin-3-ylmethylbenzenesulfonamide 4-(3-Methyl-2,4-dioxo-1-propyl-2,3,4,5-tetrahydro-1H-pyrrolo[3,2-d]pyrimidin-6-yl)-N-pyridin-4-ylmethylbenzenesulfonamide N-(6-Methoxypyridin-3-ylmethyl)-4-(3-methyl-2,4-dioxo-1-propyl-2,3,4,5-tetrahydro-1H-pyrrolo[3,2-d]pyrimidin-6-yl)benzenesulfonamide N-(3-Chloropyridin-4-ylmethyl)-4-(3-methyl-2,4-dioxo-1-propyl-2,3,4,5-tetrahydro-1H-pyrrolo[3,2-d]pyrimidin-6-yl)benzenesulfonamide N-Methyl-4-(3-methyl-2,4-dioxo-1-propyl-2,3,4,5-tetrahydro-1H-pyrrolo[3,2-d]pyrimidin-6-yl)-N-(2-pyridin-2-ylethyl)benzenesulfonamide 4-(3-Methyl-2,4-dioxo-1-propyl-2,3,4,5-tetrahydro-1H-pyrrolo[3,2-d]pyrimidin-6-yl)-N-(2-pyridin-3yl-ethyl)benzenesulfonamide 4-(3-Methyl-2,4-dioxo-1-propyl-2,3,4,5-tetrahydro-1H-pyrrolo[3,2-d]pyrimidin-6-yl)-N-(2-pyridin-4-ylethyl)benzenesulfonamide 4-(3-Methyl-2,4-dioxo-1-propyl-2,3,4,5-tetrahydro-1H-pyrrolo[3,2-d]pyrimidin-6-yl)-N-[2-(pyridin-2-yloxy)-ethyl]benzenesulfonamide 1,3-Dimethyl-6-[4-(2,3,5,6-tetrahydro-[1,2]bipyrazinyl-4-sulfonyl)phenyl]-1,5-dihydropyrrolo[3,2-d]pyrimidine-2,4-dione 4-(1-Ethyl-3-methyl-2,4-dioxo-2,3,4,5-tetrahydro-1H-pyrrolo[3,2-d]pyrimidin-6-yl)-N-pyridin-2-ylmethyl-benzenesulfonamide 4-(1-Ethyl-3methyl-2,4-dioxo-2,3,4,5-tetrahydro-1H-pyrrolo[3,2-d]pyrimidin-6-yl)-N-(2-pyridin-2-ylethyl)-benzenesulfonamide 4-(1-Ethyl-3-methyl-2,4-dioxo-2,3,4,5-tetrahydro-1H-pyrrolo[3,2-d]pyrnmidin-6-yl)-N-[2-(pyridin-2-yloxy)ethyl]-benzenesulfonamide 4-(1-Ethyl-3-methyl-2,4-dioxo-2,3,4,5-tetrahydro-1H-pyrrolo[3,2-d]pyrimidin-6-yl)-N-(6-methoxy-pyridin-3-ylmethyl)-benzenesulfonamide 4-[1,3-Bis-(3-methoxypropyl-2,4-dioxo-2,3,4,5-tetrahydro-1H-pyrrolo[3,2-d]pyrimidin-6-yl]-N-pyridin-3-ylmethyl-benzenesulphonamide 6-{4-[4-(4Bromobenzyl)-piperazine-1-sulphonyl]phenyl}-1,3-bis-(2-methoxyethyl)-1,5-dihydropyrrolo[3,2-d]pyrimidine-2,4-dione 4-[1,3-Bis-(2-methylsulphanylethyl)-2,4-dioxo-2,3,4,5-tetrahydro-1H-pyrrolo[3,2-d]pyrimidin-6-yl]-N-pyridin-4-ylmethylbenzenesulphonamide 6-{4-[4-(4-Bromobenzyl)piperazine-1-sulphonyl]phenyl}-1,3-bis-(2-methylsulphanyl-ethyl)-1,5-dihydropyrrolo[3,2-d]pyrimidine-2,4-dione {4-[4-(4-Bromobenzyl)-piperazine-1-sulphonyl]phenyl}-3-methyl-1-pyridin-4-ylmethyl-1,5-dihydro-pyrrolo[3,2-d]pyrimidine-2,4-dione N-Methyl-4-(3-methyl-2,4-dioxo-1-pyridin-4-ylmethyl-2,3,4,5-tetrahydro-1H-pyrrolo[3,2-d]pyrimidin-6-yl)-N-(2-pyridin-2-yl-ethyl)benzenesulphonamide 6-[4-(4-Benzylpiperazine-1-sulphonyl)phenyl]-3-methyl-1-phenethyl-1,5-dihydro-pyrrolo[3,2-d]pyrimidine-2,4-dione 4-(Methyl2,4-dioxo-1-phenethyl-2,3,4,5-tetrahydro1H-pyrrolo[3,2-d]pyrimidin-6-yl)-N-pyridin-2-ylmethylbenzenesulphonamide 6-[4-(4-Benzylpiperazine-1-sulphonyl)phenyl]-1,3-bis-cyclopropylmethyl-1,5-dihydro-pyrrolo[3,2-d]pyrimidine-2,4dione 4-(1,3-Bis-cyclopropylmethyl-2,4-dioxo-2,3,4,5-tetrahydro-1H-pyrrolo[3,2-d]pyrimidin-6-yl)-N-(2-pyridin-3-yl-ethyl)benzenesulphonamide 4-[2,4-Dioxo-1,3-bis-(2,2,2-trifluoroethyl)-2,3,4,5-tetrahydro-1H-pyrrolo[3,2-d]pyrimidin-6-yl]-N-(6-methoxypyridin-3-ylmethyl)benzenesulphonamide 6-[4-(4-Benzylpiperazine-1-sulphonyl)phenyl]-1,3-bis-(2,2,2-trifluoroethyl)-1,5-dihydro-pyrrolo[3,2-d]pyrimidine-2,4-dione N-(6-Methoxypyrdin-3-ylmethyl)-4-[3-methyl-1-(2-morpholin-4-yl-ethyl)-2,4-dioxo-2,3,4,5-tetrahydro-1H-pyrrolo[3,2-d]pyrimidin-6-yl]benzenesulphonamide 6-[4-(4-Benzylpiperazine-1-sulphonyl)phenyl]-3-methyl-1-(2-morpholin-4-ylethyl)-1,5-dihydropyrrolo[3,2-d]pyrimidine-2,4-dione 1-Benzyl-6-{4-[4-(4-bromobenzyl)piperazine-1-sulphonyl]phenyl}-3-methyl-1,5-dihydropyrrolo[3,2-d]pyrimidine-2,4-dione 4-(1-Benzyl-3-methyl-2,4-dioxo-2,3,4,5-tetrahydro-1H-pyrrolo[3,2-d]pyrimidin-6-yl)-N-[2-(pyridin-2-yloxy)ethyl]benzenesulphonamide 3-{6-[4-(4-Benzylpiperazine-1-sulphonyl)pheny]-3-methyl-2,4-dioxo-2,3,4,5-tetrahydro-pyrrolo[3,2-d]pyrimidin-1-yl}propionic acid methyl ester 4-[1-(3-Hydroxypropyl)-3-methyl-2,4-dioxo-2,3,4,5-tetrahydro-1H-pyrrolo[3,2-d]pyrimidin-6-yl]-N-[2-(pyridin-2-yloxy)ethyl]benzenesulphonamide 3-[4-(4-Benzylpiperazine-1-sulphonyl)phenyl]-1-cyclopentyl-3-methyl-1,5-dihydropyrrolo[3,2-d]pyrimidine-2,4-dione 4-(1-Cyclopentyl-3-methyl-2,4-dioxo-2,3,4,5-tetrahydro-1H-pyrrolo[3,2-d]pyrimidin-6-yl)-N-(2-pyridin-4-yl-ethyl)benzenesulphonamide Of outstanding interest are:

4-(1,3-Dimethyl-2,4-dioxo-2,3,4,5-tetrahydro-1H-pyrrolo[3,2-d]pyrimidin-6-yl)-N-[2-(pyridin-2-yloxy)ethyl]benzenesulfonamide 4-(1,3-Dimethyl-2,4-dioxo-2,3,4,5-tetrahydro-1H-pyrrolo[3,2-d]pyrimidin-6-yl)-N-[2-(6-methoxypyridin-2-yloxy)ethyl]benzenesulfonamide 6-[4-(4-Benzylpiperazine-1-sulphonyl)phenyl]-1,3-dimethyl-1,5-dihydropyrrolo[3,2-d]pyrimidine-2,4-dione 6-{4-[4-(4-Fluorobenzyl)piperazine-1-sulphonyl]phenyl}-1-methyl-3-propyl-1,5-dihydropyrrolo[3,2-d]pyrimidine-2,4-dione 6-[4-(4-Benzo[1,3]dioxol-5-ylmethylpiperazine-1-sulphonyl)phenyl]-1-methyl-3-propyl-1,5-dihydropyrrolo[3,2-d]pyrimidine-2,4-dione 6-{4-[4-(3-Fluorobenzyl)piperazine-1-sulphonyl]phenyl}-1,3-dimethyl-1,5-dihydropyrrolo[3,2-d]pyrimidine-2,4-dione 1-Methyl-3-propyl-6-[4-(4-pyridin-2-ylpiperazine-1-sulphonyl)phenyl]-1,5-dihydropyrrolo[3,2-d]pyrimidine-2,4-dione 4-(1,3-Dimethyl-2,4-dioxo-2,3,4,5-tetrahydro-1H-pyrrolo[3,2-d]pyrimidin-6-yl)-N-(2-pyridin-2-ylethyl)benzenesulphonamide 4-(1-Methyl-2,4-dioxo-3-propyl-2,3,4,5-tetrahydro-1H-pyrrolo[3,2-d]pyrimidin-6-yl)-N-(2-pyridin-2-ylethyl)benzenesulphonamide 4-(1,3-Dimethyl-2,4-dioxo-2,3,4,5-tetrahydro-1H-pyrrolo[3,2-d]pyrimidin-6-yl)-N-pyridin-2-ylbenzenesulphonamide 4-(1,3-Dimethyl-2,4-dioxo-2,3,4,5-tetrahydro-1H-pyrrolo[3,2-d]pyrimidin-6-yl)-N-(6-methoxypyridin-3-yl)benzenesulphonamide 6-{4-[4-(5-Chlorothiophen-2-ylmethyl)piperazine-1-sulphonyl]phenyl}-1,3-dimethyl-1,5-dihydropyrrolo[3,2-d]pyrimidine-2,4-dione 6-{4-[4-(5-Chlorothiophen-2-ylmethyl)piperazine-1-sulphonyl]phenyl}-1,3-diethyl-1,5-dihydropyrrolo[3,2-d]pyrimidine-2,4-dione N-(1-Benzylpiperidin-4-yl)-4-(2,4-dioxo-1,3-dipropyl-2,3,4,5-tetrahydro-1H-pyrrolo[3,2-d]pyrimidin-6-yl)benzenesulphonamide 4-(1,3-Diethyl-2,4-dioxo-2,3,4,5-tetrahydro-1H-pyrrolo[3,2-d]pyrimidin-6-yl)-N-[1-(4-fluorobenzyl)piperidin-4-yl]benzenesulphonamide According to a further feature of the present invention, the 4-(pyrrolopyrimidin-6-yl)benzenesulphonamide derivatives of general formula (I) are prepared by reaction of the corresponding sulphonyl chloride of formula (II):

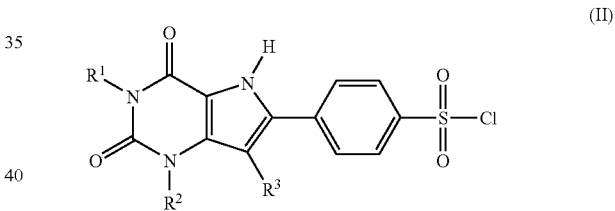

(II)

(wherein $R^1$, $R^2$ and $R^3$ are as hereinbefore defined) and the corresponding amine (III):

(III)

(wherein $R^4$ and $R^5$ are as hereinbefore defined). The reaction is carried out in an organic solvent, preferably a polar aprotic organic solvent such as dioxane, methylene chloride or tetrahydrofuran, at a temperature from 10° C. to 40° C. and in the presence of an organic base, preferably an amine base such as triethylamine or polymer supported morpholine. The thus obtained 4-(pyrrolopyrimidin-6-yl)benzenesulphonamide derivative is then isolated by standard methods known in the art.

When $R^3$ is hydrogen, the sulphonyl chloride of formula (II) is obtained from the corresponding compound of formula (IV):

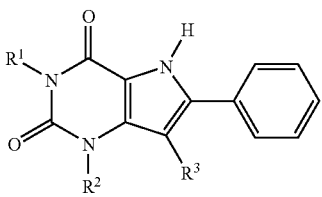

(IV)

(wherein $R^1$, $R^2$ and $R^3$ are as hereinbefore defined), by reaction with an excess of chlorosulphonic acid and optionally thionyl chloride, preferably under a nitrogen atmosphere and at a temperature from −5° C. to 10° C.

When $R^3$ is a chlorine atom, the sulphonyl chloride of formula (II) is obtained from the corresponding compound of formula (IV) by reaction with a mixture of chlorosulphonic acid and sulphuryl chloride, preferably under a nitrogen atmosphere and at a temperature from −5° C. to 10° C.

When $R^3$ is a bromine or an iodine atom, the sulphonyl chloride of formula (II) is obtained from the corresponding sulphonyl chloride of formula (II) where $R^3$ is a hydrogen atom by reaction with bromine or iodine monochloride in glacial acetic acid at room temperature.

Other substitutions at $R^3$ can be introduced by - reaction of the corresponding compounds of the general formulae (II) or (IV), or a protected version of them, with an appropiate electrophile.

The 6-phenyl-1,5-dihydropyrrolo[3,2-d]pyrimidine-2,4-dione derivatives of formula (IV) can be prepared by reaction of the corresponding 6-methyl-5-nitrouracils (V):

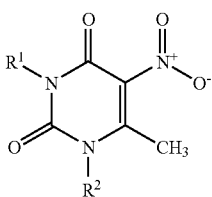

(V)

(wherein $R^1$ and $R^2$ are as hereinbefore defined), and benzaldehyde (VI):

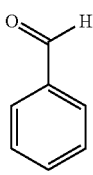

(VI)

followed by reductive cyclisation of the resulting 5-nitro-6-styryluracils by methods known in the art, e.g. C. E. Mller et al., *J. Med. Chem.* 1994, 37, 1526-1534 and references cited therein.

When the defined groups $R^1$ to $R^5$ are susceptible to chemical reaction under the conditions of the hereinbefore described processes or are incompatible with said processes, alternative processes can be readily carried out utlising organic synthetic chemistry methods to, for example, protect functional groups and finally eliminate protecting groups.

The 4-(pyrrolopyrimidin-6-yl)benzenesulphonamide derivatives of formula (I) can be converted by methods known per se into pharmaceutically acceptable salts or N-oxides.

Preferred salts are acid addition salts obtainable by treatment with organic or inorganic acids such as fumaric, tartaric, succinic or hydrochloric acid. Also 4-(pyrrolopyrimidin-6-yl)benzenesulphonamide derivatives of formula (I) in which there is the presence of an acidic group may be converted into pharmacologically acceptable salts by reaction with an alkali metal hydroxide or an organic base such as sodium or potassium hydroxide. The acid or alkali addition salts so formed may be interchanged with suitable pharmaceutically acceptable counter ions using processes known per se.

Adenosine 2B Receptor Subtype Competition Radioligand Binding

Human membranes from recombinant $A_{2B}$ receptors were purchased from Receptor Biology, Inc.(USA).

Competition assays were carried out by incubation of membranes from $hA_{2B}$ receptors transfected to HEK293 cells, [$^3$H]DPCPX as radioligand, buffer (50 mM Tris-HCl (pH 6.5), 10 mM $MgCl_2$, 1 mM EDTA, 0.1 mM benzamidine, 2 units/ml adenosine deaminase), and unlabelled ligand in a total volume of 0.1 ml for 30 min at 25° C. NECA was used to determinate non-specific binding. Filter over Schleicher&Schuell GF/52 filters (pre-soaked 0.5% polyethylenyimine) in a Brandel cell harvester. Unbound radioligand was removed with 4×2 ml ice-cold 50 mM Tris-Hcl (pH 6.5).

Adenosine 2A Receptor Subtype Competition Radioligand Binding

Human membranes from recombinant $A_{2A}$ receptors were purchased from Receptor Biology, Inc. (USA).

Competition assays were carried out by incubation of membranes from $hA_{2A}$ receptors transfected to HEK293 cells, [$^3$H]ZM241385 as radioligand, buffer (50 mM Tris-HCl (pH 7.4), 10 mM $MgCl_2$, 1 mM EDTA, 2 units/ml adenosine deaminase), and unlabelled ligand in a total volume of 0.2 ml for 90 min at 25° C. NECA was used to determinate non-specific binding. Filter over Schleicher&Schuell GF/52 filters (pre-soaked 0.5% polyethylenyimine) in a Brandel cell harvester. Unbound radioligand was removed with 3×3 ml ice-cold 50 mM Tris-Hcl 50 (pH 7.4), 0.9% NaCl.

The results are shown in Table 1 and Table 2.

TABLE 1

| Example | $IC_{50}$ $A_{2B}$ (nM) |
| --- | --- |
| 172 | 17 |
| 173 | 5 |
| 1 | 16 |
| 107 | 9 |
| 118 | 6 |
| 3 | 7 |
| 126 | 12 |
| 37 | 14 |
| 132 | 17 |
| 38 | 12 |
| 36 | 18 |
| 18 | 4 |

It can be seen from Table 1 that the compounds of formula (I) are potent inhibitors of the $A_{2B}$ adensosine receptor subtype. Preferred 4-(pyrrolopyrimidin-6-yl)benzenesulphonamide derivatives of the invention possess an $IC_{50}$ value for the inhibition of $A_{2B}$ (determined as defined above) of less than 50 nM, preferably less than 20 nM and most preferably less than 10 nM.

TABLE 2

| Example | IC$_{50}$ A$_{2A}$ (nM) |
| --- | --- |
| 18 | 85 |
| 59 | 28 |
| 38 | 75 |
| 97 | 60 |
| 69 | 84 |

It can be seen from Table 2 that the compounds of formula (I) are potent inhibitors of the A$_{2A}$ adenosine receptor subtype. Some preferred 4-(pyrrolopyrimidin-6-yl)benzenesulphonamide derivatives of the invention possess an IC$_{50}$ value for the inhibition of A$_{2A}$ (determined as defined above) of less than 100 nM and most preferably less than 50 nM.

The 4-(pyrrolopyrimidin-6-yl)benzenesulphonamide derivatives of the invention are useful in the treatment or prevention of diseases known to be susceptible to improvement by treatment with an antagonist of A$_{2A}$ and/or A$_{2B}$ adenosine receptors. For example (see WO 01/16134, WO 01/02400, WO 01/80893 or WO 00/73307), Parkinson's disease, Alzheimer's disease, Huntington chorea, Wilson's disease, asthma, bronchoconstriction. allergic diseases. inflammation, reperfusion injury, myocardial ischemia, atherosclerosis, hypertension, retinopathy, diabetes mellitus, inflammation, gastrointestinal tract disorders, and/or autoimmune diseases. Examples of autoimmune diseases which can be treated or prevented using the compounds of the invention are Addison's disease, autoimmune hemolytic anemia, Crohn's disease, Goodpasture's syndrome, Graves disease, Hashimoto's thyrolditis, idiopathic thrombocytopenic purpura, insulin-dependent diabetes mellitus, multiple sclerosis, myasthenia gravis, pemphigus vulgaris, pernicious anemia, poststreptococcal glomerulonephritis, psoriasis, rheumatoid arthritis, scleroderma, Sjogren's syndrome, spontaneous infertility, and systemic lupus erythematosus.

Accordingly, the 4-(pyrrolopyrimidinyl)benzenesulphonamide derivatives of the invention and pharmaceutically acceptable salts thereof, and pharmaceutical compositions comprising such compound and/or salts thereof, may be used in a method of treatment of disorders of the human body which comprises administering to a subject requiring such treatment an effective amount of a 4-(pyrrolopyrimidin-6-yl) benzenesulphonamide derivative of the invention or a pharmaceutically acceptable salt thereof.

The present invention also provides pharmaceutical compositions which comprise, as an active ingredient, at least a 4-(pyrrolopyrimidin6-yl)benzenesulphonamide derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound, or salts of such compound, to form the compositions of this invention are well-known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

The syntheses of the compounds of the invention and of the intermediates for use therein are illustrated by the following Examples (including Preparation Examples (Preparations 1-12)) which do not limit the scope of the invention in any way.

$^{1}$H Nuclear Magnetic Resonance Spectra were recorded on a Varian Gemini 300 spectrometer. Melting points were recorded using a Perkin Elmer DSC-7 apparatus. The chromatographic separations were obtained using a Waters 2690 system equipped with a Symmetry C18 (2.1×10 mm, 3.5 µM) column. As detectors a Micromass ZMD mass spectrometer using ES ionization and a Waters 996 Diode Array detector were used. The mobile phase was formic acid (0.46 ml), ammonia (0.115 ml) and water (1000 ml) (A) and formic acid (0.4 ml), ammonia (0.1 ml), methanol (500 ml) and acetonitrile (500 ml) (B): initially from 0% to 95% of B in 20 min. and then 4 min. with 95% of B. The reequilibration time between twNo injections was 5 min. The flow rate was 0.4 ml/min. The injection volume was 5 µl. Diode array chromatograms were processed at 210 nm.

PREPARATION EXAMPLES

Preparation 1

4-(1,3-Dimethyl-2,4-dioxo-2,3,4,5tetrahydro-1H-pyrrolo[3,2-d]pyrimidin-6-yl)-benzenesulphonyl chloride a) A mixture of 1,3,6-trimethyl-5-nitro-1H-pyrimidine-2, 4dione (3.00 g, 15.06 mmol), benzaldehyde (1.58 ml, 15.56 mmol), piperidine (1.41 ml, 15.56 mmol) and a 3 Å molecular sieve (6.00 g) in ethanol (70 ml) was refluxed for 4 hours, filtered and the solid was treated with a mixture of chloroform and methanol. The resulting suspension was filtered again and the filtrates were evaporated. The residue was triturated with diethyl ether and the precipitate collected by filtration and dried under vacuum to yield 1,3-dimethyl-5-nitro-6-((E) styryl)-1H-pyrimidine-2,4-dione (2.61 g, 60%) as a yellow solid.

b) To a stirred solution of the above compound (2.61 g, 9.08 mmol) in formic acid (80 ml) was slowly added sodium dithionite (9.30 g, 45.42 mmol) and the mixture was refluxed overnight. The resulting mixture was cooled to room temperature and it was poured into water. The precipitate was collected by filtration, washed with water and dichloromethane and then dried under vacuum to yield 1,3dimethyl-6-phenyl-1,5-dihydropyrrolo[3,2-d]pyrimidine-2,4-dione (1.54 g, 66%) as a white solid.

c) The above compound (500 mg, 1.96 mmol) was added portionwise to a mixture of chlorosulphonic acid (2.5 ml) and thionyl chloride (0.25 ml) and stirred at 0° C. for 1 hour and then at room temperature for 1 h 30 min. The reaction mixture was carefully poured into stirred ice-water and the resulting precipitate was collected by filtration, washed with water and diethyl ether and then dried under vacuum to yield the title product (607 mg, 88%) as a yellow solid.

$^1$H-NMR δ(DMSO): 12.5 (s, 1H), 7.9 (d, 2H), 7.6 (d, 2H), 6.8 (s, 1H), 3.5 (s, 3H), 3.3 (s, 3H).

Preparation 2

4-(1,3-Diethyl-2,4-dioxo-2,3,4,5-tetrahydro-1H-pyrrolo[3,2-d]pyrimidin-6-yl)benzenesulphonyl chloride Obtained as a yellow solid (29% overall) from 1,3-diethyl-6-methyl-5-nitro-1H-pyrimidine-2,4-dione following the procedure described in Preparation 1.

$^1$H-NMR δ(DMSO): 12.4 (s, 1H), 7.9 (d, 2H), 7.8 (d, 2H), 6.8 (s, 1H), 3.9 (m, 4H), 1.2 (dt, 6H).

Preparation 3

4-(2,4-Dioxo-1,3-dipropyl-2,3,4,5-tetrahydro-1H-pyrrolo[3,2-d]pyrimidin-6-yl)benzenesulphonyl chloride Obtained as a yellow solid (18% overall) from 6-methyl-5-nitro-1,3-diprbpyl-1H-pyrimidine-2,4-dione following the procedure described in Preparation 1.

$^1$H-NMR δ(DMSO): 12.2 (s, 1H), 7.9 (d, 2H), 7.6 (d, 2H), 6.8 (s, 1H), 3.9 (m, 4H), 1.6 (m, 4H), 0.9 (m, 6H).

Preparation 4

4-(1-Methyl-2,4-dioxo-3-propyl-2,3,4,5-tetrahydro-1H-pyrrolo[3,2-d]pyrimidin-6-yl)benzenesulphonyl chloride Obtained as a yellow solid (50% overall) from 1,6-dimethyl-5-nitro-3-propyl-1H-pyrimidine-2,4-dione following the procedure described in Preparation 1.

$^1$H-NMR δ(DMSO): 12.4 (s, 1H), 7.9 (d, 2H), 7.6 (d, 2H), 6.65 (s, 1H), 3.9 (t, 2H), 3.4 (s, 3H), 1.6 (m, 2H), 0.9 (t, 3H).

Preparation 5

4-(3Methyl-2,4-dioxo-1-propyl-2,3,4,5tetrahydro-1H-pyrrolo[3,2-d]pyrimidin-6-yl)benzenesulphonyl chloride Obtained as a yellow solid (40% overall) from 3,6-dimethyl-5-nitro-1-propyl-1H-pyrimidine-2,4-dione following the procedure described in Preparation 1.

$^1$H-NMR δ(DMSO): 12.4 (s, 1H), 7.9 (d, 2H), 7.6 (d, 2H), 5.8 (s,1H), 3.85 (t, 2H), 3.35 (s, 3H), 1.7 (m, 2H), 0.9 (t, 3H).

Preparation 6

4-(7-Chloro-1,3-dimethyl-2,4-dioxo-2,3,4,5-tetrahydro-1H-pyrrolo[3,2-d]pyrimidin-6-yl)benzenesulphonyl chloride The title compound of Preparation 1 (600 mg,1.69 mmol) was suspended in glacial acetic acid (6 ml), sulphuryl chloride was added dropwise (205 µl, 2.54 mmol) and the mixture was stirred at room temperature for 3 hours. The reaction mixture was then filtered, washed with dietyhl ether and dried to yield the title product as a yellow solid (384 mg, 58%).

$^1$H-NMR δ(DMSO): 12.9 (s, 1H), 7.6 (m, 4H), 3.7 (s, 3H), 3.2 (s, 3H).

EXAMPLES

TABLE 3

(I)

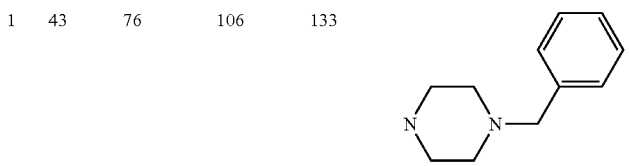

| $R^1R^2$ | | | | | |
|---|---|---|---|---|---|
| $R^1$ = Me<br>$R^2$ = Me | $R^1$ = Et<br>$R^2$ = Et | $R^1$ = nPro<br>$R^2$ = nPro | $R^1$ = nPro<br>$R^2$ = Me | $R^1$ = Me<br>$R^2$ = nPro | $NR^4R^5$ |

| Compounds of formula (I) wherein $R^3$ = H: | | | | | |
|---|---|---|---|---|---|
| 1 | 43 | 76 | 106 | 133 | 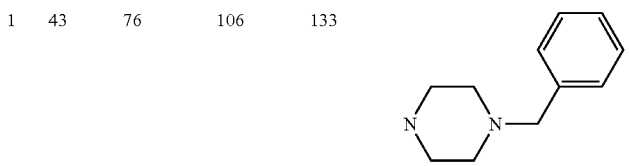 |

TABLE 3-continued
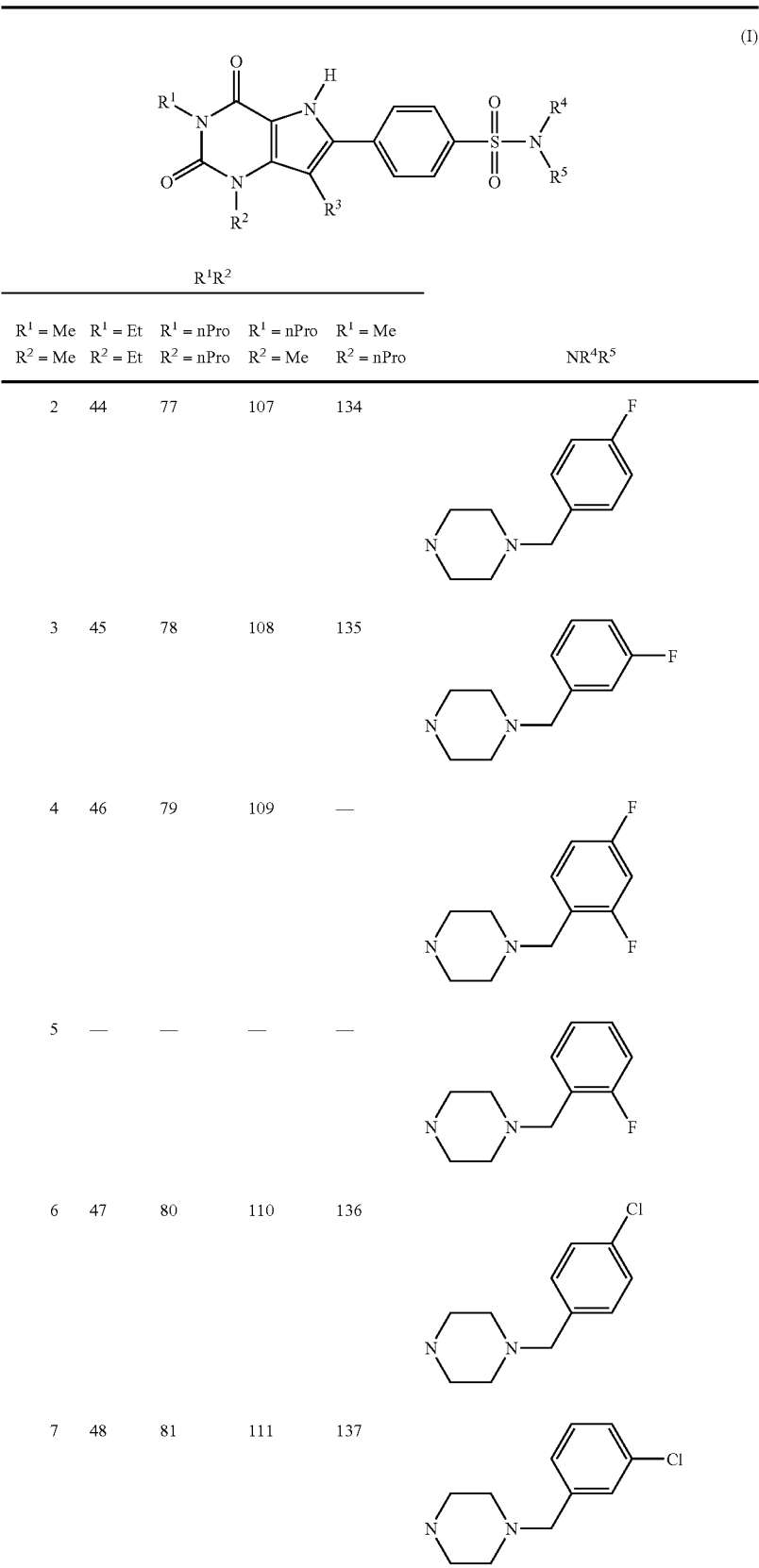
| | | R¹R² | | | |
|---|---|---|---|---|---|
| R¹ = Me R² = Me | R¹ = Et R² = Et | R¹ = nPro R² = nPro | R¹ = nPro R² = Me | R¹ = Me R² = nPro | NR⁴R⁵ |
| 2 | 44 | 77 | 107 | 134 | 4-F-benzyl-piperazine |
| 3 | 45 | 78 | 108 | 135 | 3-F-benzyl-piperazine |
| 4 | 46 | 79 | 109 | — | 2,4-diF-benzyl-piperazine |
| 5 | — | — | — | — | 2-F-benzyl-piperazine |
| 6 | 47 | 80 | 110 | 136 | 4-Cl-benzyl-piperazine |
| 7 | 48 | 81 | 111 | 137 | 3-Cl-benzyl-piperazine |

TABLE 3-continued
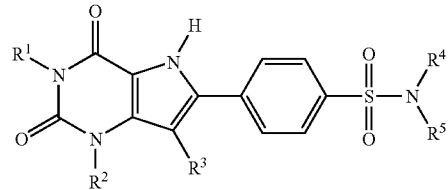
(I)
| R¹R² | | | | | | |
|---|---|---|---|---|---|---|
| R¹ = Me R² = Me | R¹ = Et R² = Et | R¹ = nPro R² = nPro | R¹ = nPro R² = Me | R¹ = Me R² = nPro | | NR⁴R⁵ |
| 8 | 49 | 82 | 112 | 138 | 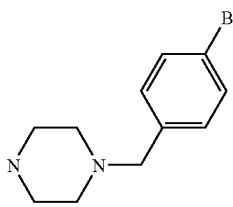 | |
| 9 | 50 | 83 | 113 | 139 | 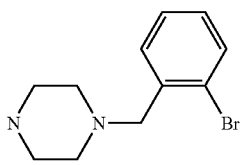 | |
| 10 | 51 | 84 | 114 | 140 | 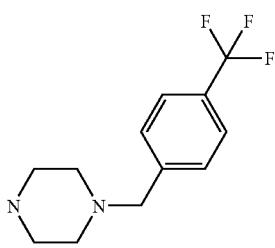 | |
| 11 | 52 | 85 | 115 | 141 | 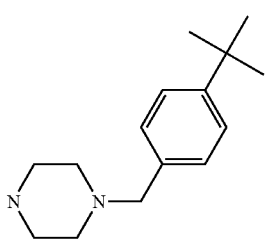 | |
| 12 | 53 | 86 | 116 | 142 | 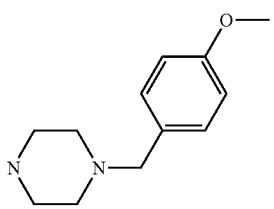 | |
| 13 | 54 | 87 | 117 | 143 | 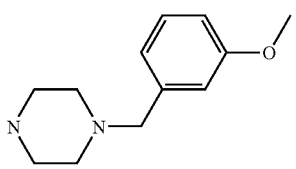 | |

TABLE 3-continued (I)

| R¹ = Me R² = Me | R¹ = Et R² = Et | R¹ = nPro R² = nPro | R¹ = nPro R² = Me | R¹ = Me R² = nPro | NR⁴R⁵ |
|---|---|---|---|---|---|
| 14 | 55 | 88 | 118 | 144 | piperazinyl-CH₂-benzo[1,3]dioxole |
| 15 | 56 | 89 | 119 | 145 | piperazinyl-CH₂-(4-cyanophenyl) |
| 16 | 57 | — | 120 | — | piperazinyl-CH₂-(3-furyl) |
| 17 | 58 | 90 | 121 | 146 | piperazinyl-CH₂-(2-thienyl) |
| 18 | 59 | 91 | 122 | 147 | piperazinyl-CH₂-(5-chloro-2-thienyl) |
| 19 | 60 | 92 | 123 | 148 | piperazinyl-CH₂-(4-pyridyl) |
| 20 | 61 | 93 | — | 149 | piperazinyl-CH(CH₃)-phenyl |

TABLE 3-continued
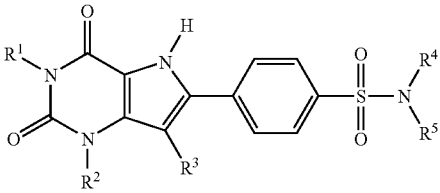
(I)
| | | R¹R² | | | |
|---|---|---|---|---|---|
| R¹ = Me R² = Me | R¹ = Et R² = Et | R¹ = nPro R² = nPro | R¹ = nPro R² = Me | R¹ = Me R² = nPro | NR⁴R⁵ |
| 21 | — | — | — | 150 | 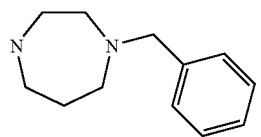 |
| 22 | 62 | 94 | 124 | 151 | 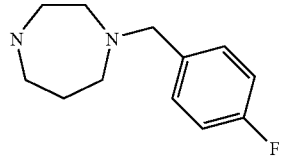 |
| — | 63 | 95 | — | 152 | 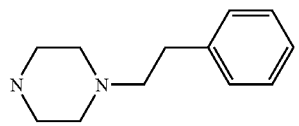 |
| 23 | — | — | — | — | 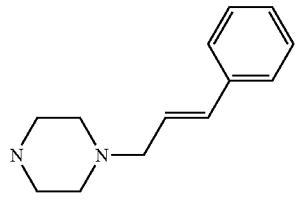 |
| 24 | 64 | — | — | 153 | 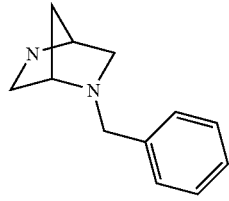 |
| 25 | — | — | — | — | 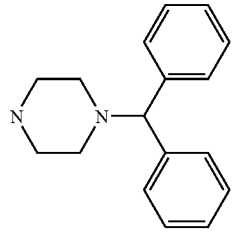 |
| 26 | 65 | — | 125 | 154 | 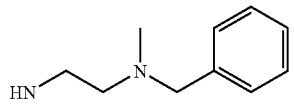 |

TABLE 3-continued
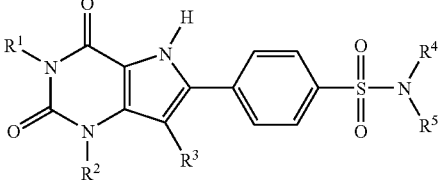
(I)
| R¹ = Me<br>R² = Me | R¹ = Et<br>R² = Et | R¹ = nPro<br>R² = nPro | R¹ = nPro<br>R² = Me | R¹ = Me<br>R² = nPro | NR⁴R⁵ |
|---|---|---|---|---|---|
| — | 66 | — | — | 155 | 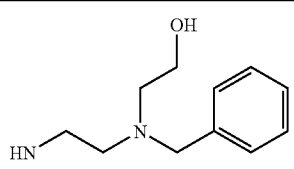 |
| 27 | 67 | 96 | 126 | 156 | 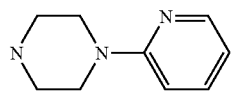 |
| 28 | — | — | — | — | 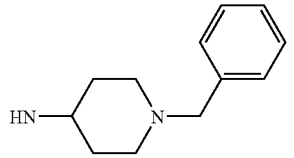 |
| 29 | 68 | 97 | 127 | 157 | 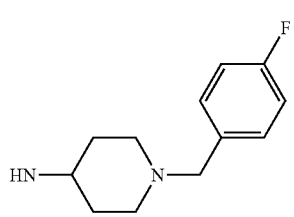 |
| 30 | 69 | 98 | 128 | 158 | 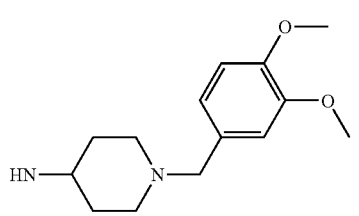 |
| 31 | 70 | 99 | 129 | 159 | 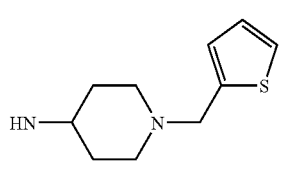 |
| 32 | 71 | 100 | 130 | 160 | |

TABLE 3-continued
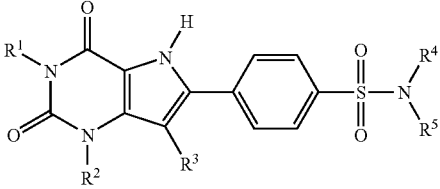
(I)
| | R¹R² | | | | |
|---|---|---|---|---|---|
| R¹ = Me R² = Me | R¹ = Et R² = Et | R¹ = nPro R² = nPro | R¹ = nPro R² = Me | R¹ = Me R² = nPro | NR⁴R⁵ |
| 33 | 72 | 101 | 131 | 161 | 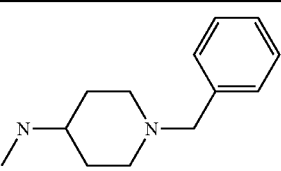 |
| 34 | 73 | 102 | — | — | 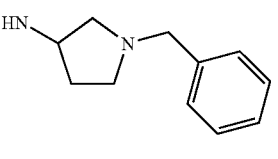 |
| 35 | 74 | — | — | — | 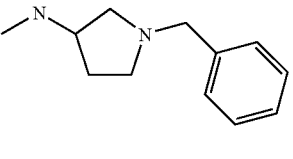 |
| 36 | — | 103 | — | — | 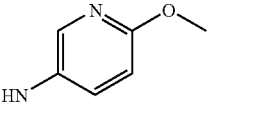 |
| 37 | 75 | 104 | 132 | 162 | 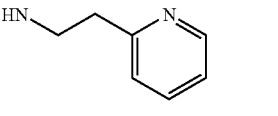 |
| 38 | — | 105 | — | — | 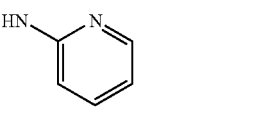 |
| 39 | — | — | — | — | 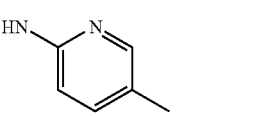 |
| 40 | — | — | — | — | 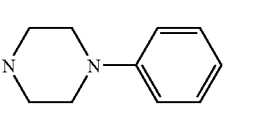 |
| 41 | — | — | — | — | 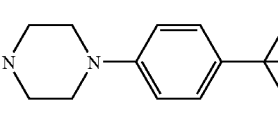 |

TABLE 3-continued
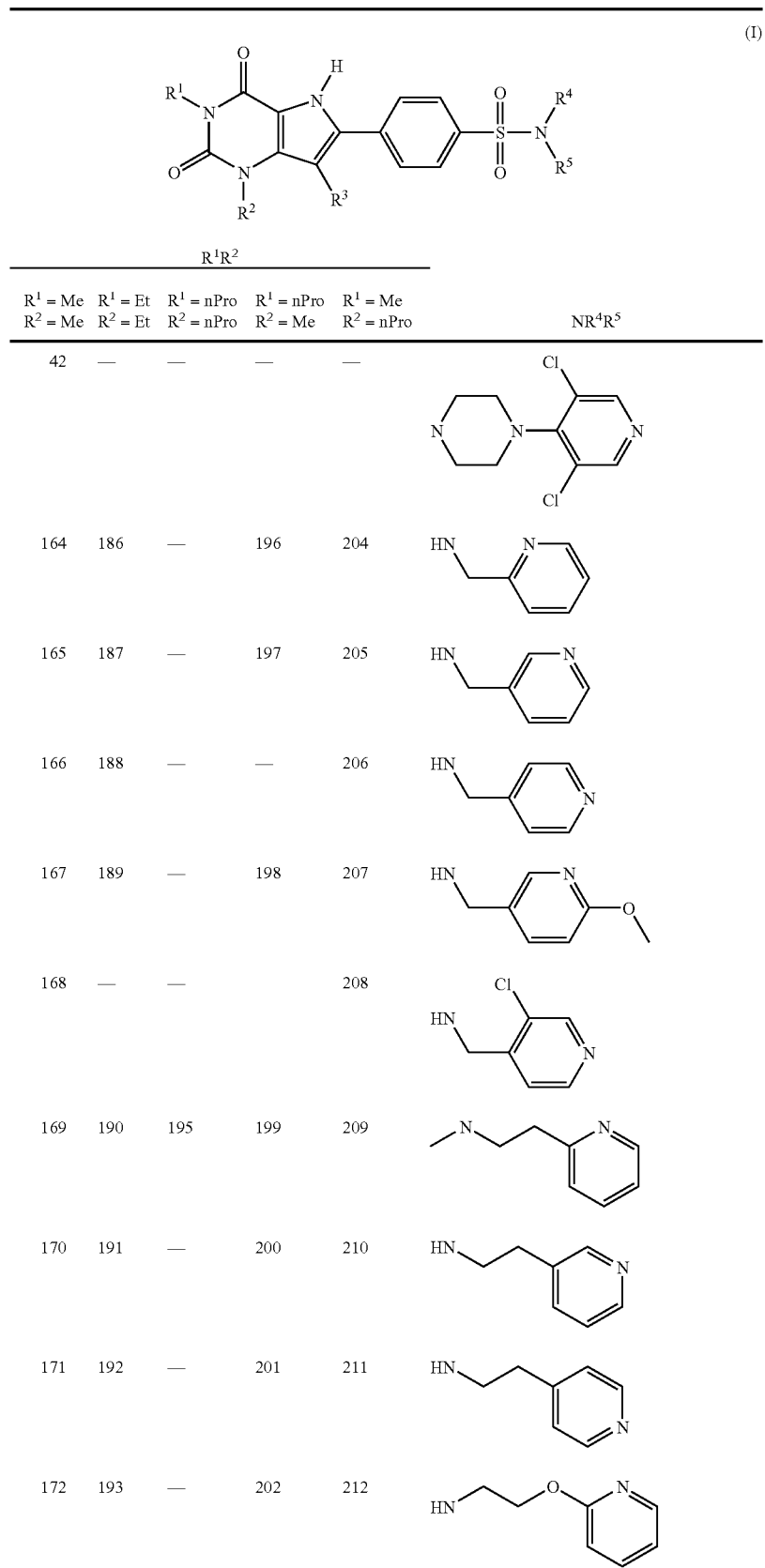
(I)
| | R¹R² | | | | |
|---|---|---|---|---|---|
| R¹ = Me R² = Me | R¹ = Et R² = Et | R¹ = nPro R² = nPro | R¹ = nPro R² = Me | R¹ = Me R² = nPro | NR⁴R⁵ |
| 42 | — | — | — | — | |
| 164 | 186 | — | 196 | 204 | |
| 165 | 187 | — | 197 | 205 | |
| 166 | 188 | — | — | 206 | |
| 167 | 189 | — | 198 | 207 | |
| 168 | — | — | — | 208 | |
| 169 | 190 | 195 | 199 | 209 | |
| 170 | 191 | — | 200 | 210 | |
| 171 | 192 | — | 201 | 211 | |
| 172 | 193 | — | 202 | 212 | |

TABLE 3-continued
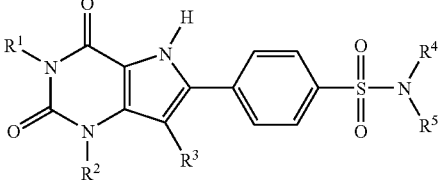
(I)
| | R¹R² | | | | |
|---|---|---|---|---|---|
| | R¹ = Me<br>R² = Me | R¹ = Et<br>R² = Et | R¹ = nPro<br>R² = nPro | R¹ = nPro<br>R² = Me | R¹ = Me<br>R² = nPro | NR⁴R⁵ |
| 173 | — | — | — | — | — | 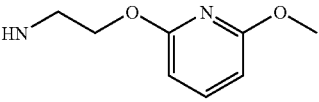 |
| 174 | — | — | — | — | — | 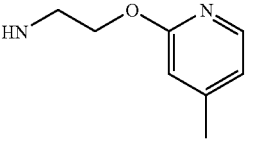 |
| 175 | — | — | — | — | — | 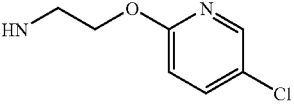 |
| 176 | — | — | — | — | — | 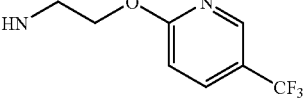 |
| 177 | — | — | — | — | — | 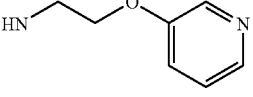 |
| 178 | — | — | — | — | — | 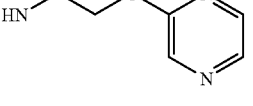 |
| 179 | — | — | — | — | — |  |
| 180 | — | — | — | — | — | 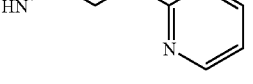 |
| 181 | 194 | — | -203 | — | — | 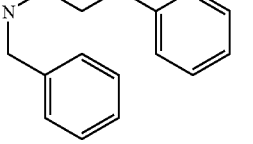 |

TABLE 3-continued

Compounds of formula (I):

| R¹R² | | | | | |
|---|---|---|---|---|---|
| R¹ = Me<br>R² = Me | R¹ = Et<br>R² = Et | R¹ = nPro<br>R² = nPro | R¹ = nPro<br>R² = Me | R¹ = Me<br>R² = nPro | NR⁴R⁵ |
| 182 — | — | — | — | — | [benzyl-N-CH2CH2-O-(6-methoxypyridin-2-yl)] |
| 183 — | — | — | — | — | [benzyl-N-CH2CH2-O-(6-chloropyridin-3-yl)] |
| 184 — | — | — | — | — | [4-(pyridin-2-ylmethyl)piperidin-1-yl] |
| 185 — | — | — | — | — | [4-(3-methoxyphenyl)piperidin-1-yl] |

Compounds of formula (I) wherein R³ = Cl:

| | | | | | |
|---|---|---|---|---|---|
| 163 — | — | — | — | — | [4-benzylpiperazin-1-yl] |

Example 1

6-[4-(4-Benzylpiperazine-1-sulphonyl)phenyl]-1,3-dimethyl-1,5-dihydropyrrolo[3,2-d]pyrimidine-2,4-dione To a mixture of the title compound of Preparation 1 (0.1 g, 0.28 mmol) and triethylamine (0.043 ml, 0.31 mmol) in dichloromethane (5 ml) was added 1-benzylpiperazine (0.054 ml, 0.31 mmol) and the resulting mixture was stirred at room temperature overnight. The reaction mixture was diluted with dichloromethene, washed with an aqueous solution of sodium bicarbonate in water, dried (MgSO₄) and evaporated under reduced pressure. The resulting crude residue was triturated with diethylether and the precipitate collected by filtration and dried under vacuum to yield the title compound (65 mg, 47%).

ESI/MS m/e: 494 ([M+H]⁺, $C_{25}H_{27}N_5O_4S$) Retention Time (min.): 6.6

Examples 2-42 and 164-185

These compounds were synthesized from the title compound of Preparation 1 following the procedure of example 1 and using the corresponding reactant. The ESI/MS data, HPLC retention times and yields are summarised in Table 4.

TABLE 4

| Example | Molecular Formula | ESI/MS m/e [M + H]$^+$ | Retention Time (min.) | Yield % |
|---|---|---|---|---|
| 2 | $C_{25}H_{26}FN_5O_4S$ | 512 | 6.5 | 52 |
| 3 | $C_{25}H_{26}FN_5O_4S$ | 512 | 7.2 | 35 |
| 4 | $C_{25}H_{25}F_2N_5O_4S$ | 530 | 7.5 | 44 |
| 5 | $C_{25}H_{26}FN_5O_4S$ | 512 | 6.9 | 85 |
| 6 | $C_{25}H_{26}ClN_5O_4S$ | 528 | 7.4 | 70 |
| 7 | $C_{25}H_{26}ClN_5O_4S$ | 528 | 7.9 | 70 |
| 8 | $C_{25}H_{26}BrN_5O_4S$ | 572 | 7.7 | 50 |
| 9 | $C_{25}H_{26}BrN_5O_4S$ | 573 | 8.8 | 56 |
| 10 | $C_{26}H_{26}F_3N_5O_4S$ | 562 | 8.6 | 74 |
| 11 | $C_{29}H_{35}N_5O_4S$ | 550 | 8.0 | 35 |
| 12 | $C_{26}H_{29}N_5O_5S$ | 524 | 5.9 | 65 |
| 13 | $C_{26}H_{29}N_5O_5S$ | 524 | 6.3 | 62 |
| 14 | $C_{26}H_{27}N_5O_6S$ | 538 | 6.5 | 58 |
| 15 | $C_{26}H_{26}N_6O_4S$ | 519 | 7.2 | 58 |
| 16 | $C_{23}H_{25}N_5O_5S$ | 484 | 5.5 | 29 |
| 17 | $C_{23}H_{25}N_5O_4S_2$ | 500 | 6.6 | 80 |
| 18 | $C_{23}H_{24}ClN_5O_4S_2$ | 535 | 8.9 | 84 |
| 19 | $C_{24}H_{26}N_6O_4S$ | 495 | 5.8 | 26 |
| 20 | $C_{26}H_{29}N_5O_4S$ | 508 | 6.2 | 50 |
| 21 | $C_{26}H_{29}N_5O_4S$ | 508 | 5.8 | 54 |
| 22 | $C_{26}H_{28}FN_5O_4S$ | 526 | 6.3 | 59 |
| 23 | $C_{27}H_{29}N_5O_4S$ | 520 | 6.5 | 58 |
| 24 | $C_{26}H_{27}N_5O_4S$ | 506 | 5.6 | 64 |
| 25 | $C_{31}H_{31}N_5O_4S$ | 570 | 10.7 | 66 |
| 26 | $C_{24}H_{27}N_5O_4S$ | 482 | 5.9 | 62 |
| 27 | $C_{23}H_{24}N_6O_4S$ | 481 | 7.1 | 58 |
| 28 | $C_{23}H_{25}N_7O_5S$ | 512 | 6.6 | 63 |
| 29 | $C_{26}H_{29}N_5O_4S$ | 508 | 5.8 | 44 |
| 30 | $C_{26}H_{28}FN_5O_4S$ | 526 | 5.9 | 60 |
| 31 | $C_{28}H_{33}N_5O_6S$ | 566 | 5.4 | 49 |
| 32 | $C_{24}H_{27}N_5O_4S_2$ | 514 | 5.3 | 54 |
| 33 | $C_{27}H_{31}N_5O_4S$ | 522 | 6.0 | 47 |
| 34 | $C_{25}H_{27}N_5O_4S$ | 494 | 5.5 | 72 |
| 35 | $C_{26}H_{29}N_5O_4S$ | 508 | 5.7 | 74 |
| 36 | $C_{20}H_{19}N_5O_5S$ | 442 | 8.0 | 84 |
| 37 | $C_{21}H_{21}N_5O_4S$ | 440 | 5.5 | 54 |
| 38 | $C_{19}H_{17}N_5O_4S$ | 412 | 6.6 | 52 |
| 39 | $C_{20}H_{19}N_5O_4S$ | 526 | 6.4 | 24 |
| 40 | $C_{24}H_{25}N_5O_4S$ | 480 | 9.4 | 81 |
| 41 | $C_{25}H_{24}F_3N_5O_4S$ | 548 | 10.2 | 26 |
| 42 | $C_{23}H_{22}Cl_2N_6O_4S$ | 550 | 9.5 | 48 |
| 164 | $C_{20}H_{19}N_5O_4S$ | 426 | 6.4 | 45 |
| 165 | $C_{20}H_{19}N_5O_4S$ | 426 | 5.7 | 82 |
| 166 | $C_{20}H_{19}N_5O_4S$ | 426 | 5.3 | 44 |
| 167 | $C_{21}H_{21}N_5O_5S$ | 456 | 7.2 | 52 |
| 168 | $C_{20}H_{18}ClN_5O_4S$ | 461 | 7.3 | 25 |
| 169 | $C_{22}H_{23}N_5O_4S$ | 455 | 6.0 | 15 |
| 170 | $C_{21}H_{21}N_5O_4S$ | 440 | 5.4 | 58 |
| 171 | $C_{21}H_{21}N_5O_4S$ | 440 | 5.1 | 65 |
| 172 | $C_{21}H_{21}N_5O_5S$ | 456 | 7.3 | 66 |
| 173 | $C_{22}H_{23}N_5O_6S$ | 487 | 8.1 | 89 |
| 174 | $C_{22}H_{23}N_5O_5S$ | 471 | 7.6 | 90 |
| 175 | $C_{21}H_{20}ClN_5O_5S$ | 491 | 8.3 | 91 |
| 176 | $C_{22}H_{20}F_3N_5O_5S$ | 524 | 8.5 | 65 |
| 177 | $C_{21}H_{21}N_5O_5S$ | 456 | 5.8 | 85 |
| 178 | $C_{20}H_{20}N_6O_5S$ | 457 | 6.9 | 68 |
| 179 | $C_{21}H_{21}N_5O_4S_2$ | 473 | 7.8 | 75 |
| 180 | $C_{20}H_{20}N_6O_4S_2$ | 474 | 7.1 | 65 |
| 181 | $C_{28}H_{27}N_5O_5S$ | 547 | 9.3 | 44 |
| 182 | $C_{29}H_{29}N_5O_6S$ | 577 | 10.1 | 74 |
| 183 | $C_{28}H_{26}ClN_5O_5S$ | 581 | 9.4 | 74 |
| 184 | $C_{26}H_{28}N_4O_4S$ | 494 | 9.8 | 54 |
| 185 | $C_{26}H_{28}N_4O_5S$ | 510 | 9.3 | 49 |

Example 172

δ $^1$H NMR (DMSO): 12.65 (bs, 1H), 8.18 (d, 2H), 7.95 (t, 1H), 7.82 (d, 2H), 7.66 (dd, 1H), 6.98 (t, 1H), 6.9 (s, 1H), 6.75 (d, 1H), 4.22 (t, 2H), 3.43 (s, 3H), 3.25 (s, 3H), 3.21 (q, 2H).

Example 173

δ $^1$H NMR (DMSO): 8.05 (d, 2H), 7.85 (d, 2H), 7.50 (t, 1H), 6.90 (s, 1H), 6.25 (t, 2H), 4.20 (m, 2H), 3.80 (s, 3H), 3.45 (s, 3H), 3.35 (m, 2H), 3.15 (s, 3H), 3.05 (s, 3H).

Examples 43-75 and 186-194

These compounds were synthesized from the title oompound of Preparation 2 following the procedure of example 1 and using the corresponding reactant. The ESI/MS data, HPLC retention times and yields are summrarised in Table 5.

TABLE 5

| Example | Molecular Formula | ESI/MS m/e [M + H]$^+$ | Retention Time (min.) | Yield % |
|---|---|---|---|---|
| 43 | $C_{27}H_{31}N_5O_4S$ | 522 | 7.1 | 20 |
| 44 | $C_{27}H_{30}FN_5O_4S$ | 540 | 7.5 | 70 |
| 45 | $C_{27}H_{30}FN_5O_4S$ | 540 | 8.3 | 62 |
| 46 | $C_{27}H_{29}F_2N_5O_4S$ | 558 | 8.6 | 65 |
| 47 | $C_{27}H_{30}ClN_5O_4S$ | 556 | 8.6 | 48 |
| 48 | $C_{27}H_{30}ClN_5O_4S$ | 556 | 9.1 | 77 |
| 49 | $C_{27}H_{30}BrN_5O_4S$ | 601 | 8.9 | 76 |
| 50 | $C_{27}H_{30}BrN_5O_4S$ | 601 | 9.9 | 63 |
| 51 | $C_{28}H_{30}F_3N_5O_4S$ | 590 | 9.6 | 60 |
| 52 | $C_{31}H_{39}N_5O_4S$ | 578 | 8.9 | 58 |
| 53 | $C_{28}H_{33}N_5O_5S$ | 552 | 6.7 | 70 |
| 54 | $C_{28}H_{33}N_5O_5S$ | 552 | 7.2 | 36 |
| 55 | $C_{28}H_{31}N_5O_6S$ | 566 | 6.9 | 44 |
| 56 | $C_{28}H_{30}N_6O_4S$ | 547 | 8.3 | 50 |
| 57 | $C_{25}H_{29}N_5O_5S$ | 512 | 6.3 | 50 |
| 58 | $C_{25}H_{29}N_5O_4S_2$ | 528 | 7.7 | 66 |
| 59 | $C_{25}H_{28}ClN_5O_4S_2$ | 562 | 9.8 | 74 |
| 60 | $C_{26}H_{30}N_6O_4S$ | 523 | 6.7 | 39 |
| 61 | $C_{28}H_{33}N_5O_4S$ | 536 | 7.0 | 28 |
| 62 | $C_{28}H_{32}N_5O_4S$ | 554 | 6.6 | 80 |
| 63 | $C_{28}H_{33}N_5O_4S$ | 536 | 6.8 | 62 |
| 64 | $C_{28}H_{31}N_5O_4S$ | 534 | 6.2 | 57 |
| 65 | $C_{26}H_{31}N_5O_4S$ | 510 | 6.2 | 47 |
| 66 | $C_{27}H_{33}N_5O_5S$ | 540 | 6.2 | 60 |
| 67 | $C_{25}H_{28}N_6O_4S$ | 509 | 7.8 | 56 |
| 68 | $C_{28}H_{33}N_5O_4S$ | 536 | 6.1 | 70 |
| 69 | $C_{28}H_{32}FN_5O_4S$ | 554 | 6.2 | 63 |
| 70 | $C_{30}H_{37}N_5O_6S$ | 596 | 6.0 | 51 |
| 71 | $C_{26}H_{31}N_5O_4S_2$ | 542 | 6.0 | 74 |
| 72 | $C_{29}H_{35}N_5O_4S$ | 550 | 6.3 | 38 |
| 73 | $C_{27}H_{31}N_5O_4S$ | 522 | 6.0 | 32 |
| 74 | $C_{28}H_{33}N_5O_4S$ | 536 | 6.3 | 87 |
| 75 | $C_{23}H_{25}N_5O_4S$ | 468 | 6.5 | 36 |
| 186 | $C_{22}H_{23}N_5O_4S$ | 455 | 7.4 | 54 |
| 187 | $C_{22}H_{23}N_5O_4S$ | 455 | 6.7 | 86 |
| 188 | $C_{22}H_{23}N_5O_4S$ | 455 | 6.2 | 85 |
| 189 | $C_{23}H_{25}N_5O_5S$ | 485 | 8.1 | 75 |
| 190 | $C_{24}H_{27}N_5O_4S$ | 483 | 7.0 | 74 |
| 191 | $C_{23}H_{25}N_5O_4S$ | 469 | 6.3 | 61 |
| 192 | $C_{23}H_{25}N_5O_4S$ | 469 | 6.0 | 80 |
| 193 | $C_{23}H_{25}N_5O_5S$ | 485 | 8.2 | 58 |
| 194 | $C_{30}H_{31}N_5O_5S$ | 575 | 9.9 | 65 |

Examples 76-105 and 195

These compounds were synthesized from the title compound of Preparation 3 following the procedure of example 1 and using the corresponding reactant. The ESI/MS data, HPLC retention times and yields are summarised in Table 6.

TABLE 6

| Example | Molecular Formula | ESI/MS m/e [M + H]+ | Retention Time (min.) | Yield % |
|---|---|---|---|---|
| 76 | $C_{29}H_{35}N_5O_4S$ | 550 | 8.4 | 60 |
| 77 | $C_{29}H_{34}FN_5O_4S$ | 568 | 8.7 | 74 |
| 78 | $C_{29}H_{34}FN_5O_4S$ | 568 | 9.5 | 90 |
| 79 | $C_{29}H_{33}F_2N_5O_4S$ | 586 | 9.7 | 58 |
| 80 | $C_{29}H_{34}ClN_5O_4S$ | 586 | 9.9 | 57 |
| 81 | $C_{29}H_{34}ClN_5O_4S$ | 585 | 10.2 | 39 |
| 82 | $C_{29}H_{34}BrN_5O_4S$ | 629 | 10.1 | 58 |
| 83 | $C_{29}H_{34}BrN_5O_4S$ | 629 | 10.8 | 64 |
| 84 | $C_{30}H_{34}F_3N_5O_4S$ | 618 | 10.5 | 68 |
| 85 | $C_{33}H_{43}N_5O_4S$ | 606 | 10.1 | 75 |
| 86 | $C_{30}H_{37}N_5O_5S$ | 580 | 7.7 | 49 |
| 87 | $C_{30}H_{37}N_5O_5S$ | 580 | 8.4 | 31 |
| 88 | $C_{30}H_{35}N_5O_6S$ | 594 | 7.9 | 54 |
| 89 | $C_{30}H_{34}N_6O_4S$ | 575 | 9.4 | 52 |
| 90 | $C_{27}H_{33}N_5O_4S_2$ | 556 | 9.0 | 61 |
| 91 | $C_{27}H_{32}ClN_5O_4S_2$ | 592 | 10.6 | 25 |
| 92 | $C_{28}H_{34}N_6O_4S$ | 551 | 7.9 | 74 |
| 93 | $C_{30}H_{37}N_5O_4S$ | 564 | 8.2 | 52 |
| 94 | $C_{30}H_{36}FN_5O_4S$ | 582 | 7.4 | 70 |
| 95 | $C_{30}H_{37}N_5O_4S$ | 564 | 7.8 | 69 |
| 96 | $C_{27}H_{32}N_6O_4S$ | 537 | 9.0 | 33 |
| 97 | $C_{30}H_{37}N_5O_4S$ | 564 | 6.9 | 30 |
| 98 | $C_{30}H_{36}FN_5O_4S$ | 582 | 6.9 | 55 |
| 99 | $C_{32}H_{41}N_5O_6S$ | 624 | 6.8 | 80 |
| 100 | $C_{28}H_{35}N_5O_4S_2$ | 570 | 6.7 | 77 |
| 101 | $C_{31}H_{39}N_5O_4S$ | 578 | 7.1 | 29 |
| 102 | $C_{29}H_{35}N_5O_4S$ | 550 | 6.8 | 38 |
| 103 | $C_{24}H_{27}N_5O_5S$ | 498 | 9.2 | 49 |
| 104 | $C_{25}H_{29}N_5O_4S$ | 496 | 7.8 | 54 |
| 105 | $C_{23}H_{25}N_5O_4S$ | 468 | 8.1 | 66 |
| 195 | $C_{26}H_{31}N_5O_4S$ | 511 | 8.4 | 71 |

Examples 106-132 and 196-203

These compounds were synthesized from the title compound of Preparation 4 following the procedure of example 1 and using the corresponding reactant. The ESI/MS data, HPLC retention times and yields are summarised in Table 7.

TABLE 7

| Example | Molecular Formula | ESI/MS m/e [M + H]+ | Retention Time (min.) | Yield % |
|---|---|---|---|---|
| 106 | $C_{27}H_{31}N_5O_4S$ | 522 | 7.2 | 70 |
| 107 | $C_{27}H_{30}FN_5O_4S$ | 540 | 7.6 | 66 |
| 108 | $C_{27}H_{30}FN_5O_4S$ | 540 | 8.2 | 29 |
| 109 | $C_{27}H_{29}F_2N_5O_4S$ | 558 | 8.5 | 27 |
| 110 | $C_{27}H_{30}ClN_5O_4S$ | 557 | 8.6 | 35 |
| 111 | $C_{27}H_{30}ClN_5O_4S$ | 556 | 9.2 | 57 |
| 112 | $C_{27}H_{30}BrN_5O_4S$ | 601 | 8.9 | 84 |
| 113 | $C_{27}H_{30}BrN_5O_4S$ | 601 | 9.9 | 48 |
| 114 | $C_{28}H_{30}F_3N_5O_4S$ | 590 | 9.6 | 41 |
| 115 | $C_{31}H_{39}N_5O_4S$ | 578 | 8.9 | 32 |
| 116 | $C_{28}H_{33}N_5O_5S$ | 552 | 6.7 | 58 |
| 117 | $C_{28}H_{33}N_5O_5S$ | 552 | 7.3 | 51 |
| 118 | $C_{28}H_{31}N_5O_6S$ | 566 | 6.9 | 55 |
| 119 | $C_{28}H_{30}N_6O_4S$ | 547 | 8.3 | 64 |
| 120 | $C_{25}H_{29}N_5O_5S$ | 512 | 6.3 | 35 |
| 121 | $C_{25}H_{29}N_5O_4S_2$ | 528 | 7.7 | 48 |
| 122 | $C_{25}H_{28}ClN_5O_4S_2$ | 563 | 9.8 | 54 |
| 123 | $C_{26}H_{30}N_6O_4S$ | 523 | 6.7 | 59 |
| 124 | $C_{28}H_{32}FN_5O_4S$ | 554 | 6.6 | 65 |
| 125 | $C_{26}H_{31}N_5O_4S$ | 510 | 6.3 | 80 |
| 126 | $C_{25}H_{28}N_6O_4S$ | 509 | 7.8 | 47 |
| 127 | $C_{28}H_{33}N_5O_4S$ | 536 | 6.1 | 81 |
| 128 | $C_{28}H_{32}FN_5O_4S$ | 554 | 6.3 | 56 |
| 129 | $C_{30}H_{37}N_5O_6S$ | 596 | 6.1 | 63 |
| 130 | $C_{26}H_{31}N_5O_4S_2$ | 542 | 6.1 | 65 |
| 131 | $C_{29}H_{35}N_5O_4S$ | 550 | 6.4 | 68 |

TABLE 7-continued

| Example | Molecular Formula | ESI/MS m/e [M + H]+ | Retention Time (min.) | Yield % |
|---|---|---|---|---|
| 132 | $C_{23}H_{25}N_5O_4S$ | 468 | 6.6 | 64 |
| 196 | $C_{22}H_{23}N_5O_4S$ | 455 | 7.4 | 85 |
| 197 | $C_{22}H_{23}N_5O_4S$ | 455 | 6.8 | 84 |
| 198 | $C_{23}H_{25}N_5O_5S$ | 485 | 8.1 | 66 |
| 199 | $C_{24}H_{27}N_5O_4S$ | 483 | 7.1 | 91 |
| 200 | $C_{23}H_{25}N_5O_4S$ | 469 | 6.4 | 45 |
| 201 | $C_{23}H_{25}N_5O_4S$ | 469 | 6.0 | 30 |
| 202 | $C_{23}H_{25}N_5O_5S$ | 485 | 8.2 | 57 |
| 203 | $C_{30}H_{31}N_5O_5S$ | 575 | 10.0 | 66 |

Examples 133-162 and 204-212

These compounds were synthesized from the title compound of Preparation 5 following the procedure of example 1 and using the corresponding reactant. The ESI/MS data, HPLC retention times and yields are summarised in Table 8.

TABLE 8

| Example | Molecular Formula | ESI/MS m/e [M + H]+ | Retention Time (min.) | Yield % |
|---|---|---|---|---|
| 133 | $C_{27}H_{31}N_5O_4S$ | 522 | 7.3 | 45 |
| 134 | $C_{27}H_{30}FN_5O_4S$ | 540 | 7.5 | 49 |
| 135 | $C_{27}H_{30}FN_5O_4S$ | 540 | 8.5 | 58 |
| 136 | $C_{27}H_{30}ClN_5O_4S$ | 556 | 8.8 | 84 |
| 137 | $C_{27}H_{30}ClN_5O_4S$ | 556 | 9.3 | 29 |
| 138 | $C_{27}H_{30}BrN_5O_4S$ | 601 | 9.0 | 28 |
| 139 | $C_{27}H_{30}BrN_5O_4S$ | 601 | 10.0 | 56 |
| 140 | $C_{28}H_{30}F_3N_5O_4S$ | 590 | 9.7 | 45 |
| 141 | $C_{31}H_{39}N_5O_4S$ | 578 | 9.1 | 54 |
| 142 | $C_{28}H_{33}N_5O_5S$ | 552 | 6.8 | 48 |
| 143 | $C_{28}H_{33}N_5O_5S$ | 552 | 7.4 | 50 |
| 144 | $C_{28}H_{31}N_5O_6S$ | 566 | 7.1 | 72 |
| 145 | $C_{28}H_{30}N_6O_4S$ | 547 | 8.4 | 77 |
| 146 | $C_{25}H_{29}N_5O_4S_2$ | 528 | 7.8 | 66 |
| 147 | $C_{25}H_{28}ClN_5O_4S_2$ | 562 | 9.8 | 36 |
| 148 | $C_{26}H_{30}N_5O_4S$ | 523 | 6.8 | 39 |
| 149 | $C_{28}H_{33}N_5O_4S$ | 536 | 7.1 | 47 |
| 150 | $C_{28}H_{33}N_5O_4S$ | 536 | 6.5 | 78 |
| 151 | $C_{28}H_{32}FN_5O_4S$ | 554 | 6.7 | 59 |
| 152 | $C_{28}H_{33}N_5O_4S$ | 536 | 6.9 | 66 |
| 153 | $C_{28}H_{31}N_5O_4S$ | 534 | 6.3 | 60 |
| 154 | $C_{28}H_{31}N_5O_4S$ | 510 | 6.3 | 69 |
| 155 | $C_{27}H_{33}N_5O_5S$ | 540 | 6.3 | 49 |
| 156 | $C_{25}H_{28}N_8O_4S$ | 509 | 7.8 | 75 |
| 157 | $C_{28}H_{33}N_5O_4S$ | 536 | 6.2 | 38 |
| 158 | $C_{28}H_{32}FN_5O_4S$ | 554 | 6.2 | 24 |
| 159 | $C_{30}H_{37}N_5O_6S$ | 596 | 6.0 | 62 |
| 160 | $C_{28}H_{31}N_5O_4S_2$ | 542 | 6.0 | 50 |
| 161 | $C_{29}H_{35}N_5O_4S$ | 550 | 6.4 | 47 |
| 162 | $C_{23}H_{25}N_5O_4S$ | 468 | 6.6 | 58 |
| 204 | $C_{22}H_{23}N_5O_4S$ | 455 | 7.5 | 45 |
| 205 | $C_{22}H_{23}N_5O_4S$ | 455 | 6.9 | 58 |
| 206 | $C_{22}H_{23}N_5O_4S$ | 455 | 6.4 | 91 |
| 207 | $C_{23}H_{25}N_5O_5S$ | 485 | 8.2 | 75 |
| 208 | $C_{22}H_{22}ClN_5O_4S$ | 489 | 8.2 | 71 |
| 209 | $C_{24}H_{27}N_5O_4S$ | 483 | 7.2 | 84 |
| 210 | $C_{23}H_{25}N_5O_4S$ | 469 | 6.4 | 58 |
| 211 | $C_{23}H_{25}N_5O_4S$ | 469 | 6.0 | 66 |
| 212 | $C_{23}H_{25}N_5O_5S$ | 485 | 8.3 | 62 |

Example 163

This compound was synthesized from the title compound of Preparation 6 and from 1-benzylpiperazine following the procedure of example 1.
ESI/MS m/e: 529 ([M+H]+, $C_{25}H_{26}ClN_5O_4S$) Retention Time (min.): 7.4

The following examples illustrate pharmaceutical compositions according to the present invention and procedure for their preparation.

Composition Example 1

50,000 capsules each containing 100 mg of 3-methyl-6-[5-(4-methylpiperazine-1-sulphonyl)-2-propoxyphenyl]-1-propyl-1,5-dihydropyrrolo[3,2-d]pyrimidine-2,4-dione (active ingredient) were prepared according to the following formulation:

| Active ingredient | 5 Kg |
|---|---|
| Lactose monohydrate | 10 Kg |
| Colloidal silicon dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 tablets each containing 50 mg of 6-[5-(ethylpiperazine-1-sulphonyl)-2-propoxyphenyl]-3-methyl-1-propyl-1,5-dihydropyrrolo[3,2-d]pyrimidine-2,4dione (active ingredient) were prepared from the following formulation:

| Active ingredient | 2.5 Kg |
|---|---|
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc. and flat bevelled punches. The disintegration time of the tablets was about 3 minutes.

The invention claimed is:

1. A compound of formula (I)

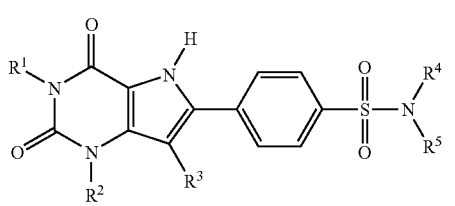

wherein $R^1$ and $R^2$ each independently represents:
a) a hydrogen atom;
b) a hydrocarbon chain chosen from an alkyl, alkenyl and alkynyl groups, wherein said hydrocarbon chain is optionally substituted by one or more substituents chosen from halogen, hydroxy, alkoxy, alkylthio, amino, monoalkylamino, dialkylamino, cyano, oxo, hydroxycarbonyl, alkoxycarbonyl, acylamino, carbamoyl, alkylcarbamoyl, dihydroxyphosphoryloxy and dialkoxyphosphoryloxy groups; or
c) a group of formula —$(CH_2)_n$—$R^6$ n is an integer from 0 to 4 and
$R^6$ represents a 3- to 7-membered aromatic or non-aromatic cyclic group containing from 0 to 4 heteroatoms chosen from N, O and S, wherein said 3- to 7-membered aromatic or non-aromatic cyclic group is optionally bridged and/or fused to another 3- to 7-membered aromatic or non-aromatic cyclic group containing from 0 to 4 heteroatoms chosen from N, O and S; and
wherein each of the cyclic groups in the moiety $R^6$ being is independently optionally substituted by one or more $R^7$ substituents;
$R^7$ represents a group chosen from halogen, alkyl, alkenyl, alkynyl, aryl, arylalkyl, cycloalkyl, heteroaryl, heteroarylalkyl, heterocyclyl, hydroxy, alkylenedioxy, alkoxy, alkylthio, amino, monoalkylamino, dialkylamino, nitro, cyano, oxo, hydroxycarbonyl, alkoxycarbonyl, acylamino, carbamoyl, alkylcarbamoyl, dihydroxyphosphoryloxy and dialkoxyphosphoryloxy groups;
wherein each of the hydrocarbon chains and each of the cyclic moieties in $R^7$ is independently optionally substituted by one or more further $R^8$ substituents,
$R^8$ represents a group chosen from halogen, hydroxy, oxo, cyano, alkyl, difluoromethyl, trifluoromethyl, alkoxy, alkylenedioxy, alkylthio acylamino, carbamoyl, alkylcarbamoyl, dihydroxyphosphoryloxy, dialkoxyphosphoryloxy, hydroxyalkoxy, phenyl, alkoxycarbonyl, amino, monoalkylamino, dialkylamino and hydroxycarbonyl groups;
$R^3$ represents a hydrogen or halogen atom, or a nitro, alkoxycarbonyl or alkyl group; wherein the alkyl group is optionally substituted by one or more substituents chosen from hydroxy, alkoxy, alkylthio, amino, monoalkylamino, dialkylamino, hydroxycarbonyl, alkoxycarbonyl, acylamino, carbamoyl sand alkylcarbamoyl groups;
$R^4$ and $R^5$ are the same or different, each independently representing:
a) hydrogen;
b) a group of formula —$(CH_2)_n$—$R^6$;
c) or a hydrocarbon chain chosen from alkyl, alkenyl and alkynyl, wherein said hydrocarbon chain is optionally substituted by one or more substituents chosen from —$(CH_2)_n$—$R^6$, —O—$(CH_2)_n$—$R^6$, —S—$(CH_2)_n$—$R^6$, —NH—$(CH_2)_n$—$R^6$, hydroxy, oxo, halogen, alkoxy, alkylthio, amino, monoalkylamino, and dialkylamino groups; wherein each of the alkyl chains in the alkoxy, alkylthio, monoalkylamino or dialkylamino substituents is independently optionally substituted by one or more further substituents chosen from —$(CH_2)_n$—$R^6$, hydroxy, oxo, halogen, alkoxy, alkylthio, amino, monoalkylamino and dialkylamino groups; wherein each n is independently an integer from 0 to 4 and each $R^6$ is independently chosen from each other; or
d) alternatively, $R^4$ and $R^5$, together with the nitrogen atom to which they are attached, form a 3- to 7-membered aromatic or non-aromatic cyclic group containing from 1 to 4 heteroatoms chosen from N, O and S, wherein said 3- to 7-membered aromatic or non-aromatic cyclic group is optionally bridged and/or fused to another 3- to 7-membered aromatic or non-aromatic cyclic group containing from 0 to 4 heteroatoms chosen from N, O and S;
wherein each of the cyclic groups is independently optionally substituted by one or more substituents chosen from —$(CH_2)_n R^6$ and $R^7$; wherein each of the hydrocarbon chains and each of the cyclic moieties of the $R^7$ substituents is independently optionally substituted by one or more further substituents chosen from—$(CH_2)_n$—$R^6$ and $R^8$; wherein each of the alkyl chains in the $R^8$ substituents is independently optionally substituted by one or more further substitutents chosen from —$(CH_2)_n$—$R^6$, hydroxy, halogen, alkoxy, alkylthio, amino, monoalkylamino and dialkylamino groups; wherein each of the $R^6$ substituents is independently chosen from each other;
or an N-oxide or a pharmaceutically acceptable salt thereof.

2. A compound according to claim 1, wherein each of $R^1$ and $R^2$ independently represents:
a) an alkyl group optionally substituted by one or more substituents chosen from hydroxy, halogen, alkoxy, alkylthio, amino, monoalkylamino, dialkylamino, hydroxycarbonyl, and alkoxycarbonyl groups; or
b) a group of formula —$(CH_2)_n$—$R^6$, wherein n is an integer from 0 to 2 and $R^6$ represents a 3- to 7-membered aromatic or non-aromatic cyclic group having from 0 to 2 heteroatoms chosen from nitrogen and oxygen.

3. A compound according to claim 2 wherein $R^1$ and $R^2$ are both unsubstituted $C_1$-$C_6$ alkyl groups.

4. A compound according to claim 1, wherein $R^3$ represents hydrogen or a halogen atom.

5. A compound according to claim 1, wherein
$R^5$ is hydrogen, a group of formula —$(CH_2)_n R^6$ or a hydrocarbon chain chosen from alkyl, alkenyl and alkynyl, wherein said hydrocarbon chain is optionally substituted by one or more groups chosen from —$(CH_2)_n$—$R^6$ and —O—$(CH_2)_n$—$R^6$;
wherein each $R^6$ is independently a phenyl or a pyridyl group, and
wherein each $R^6$ is independently optionally substituted by one or more substituents chosen from halogen, hydroxy, alkyl, alkoxy and alkylthio groups.

6. A compound according to claim 5, wherein $R^5$ is hydrogen or an alkyl group.

7. A compound of formula (I)

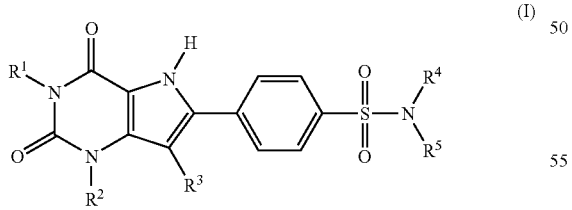

wherein
$R^1$ and $R^2$ each independently represents:
a) hydrogen atom;
b) hydrocarbon chain chosen from an alkyl, alkenyl and alkynyl groups, wherein said hydrocarbon chain is optionally substituted by one or more substituents chosen from halogen, hydroxy, alkoxy, alkylthio, amino, monoalkylamino, dialkylamino, cyano, oxo, hydroxycarbonyl, alkoxycarbonyl, acylamino, carbamoyl, alkylcarbamoyl, dihydroxyphosphoryloxy and dialkoxyphosphoryloxy groups; or
c) a group of formula —$(CH_2)_n$—$R^6$ n is an integer from 0 to 4 and
$R^6$ represents a 3- to 7-membered aromatic or non-aromatic cyclic group containing from 0 to 4 heteroatoms chosen from N, O and S, wherein said 3- to 7-membered aromatic or non-aromatic cyclic group is optionally bridged and/or fused to another 3- to 7-membered aromatic or non-aromatic cyclic group containing from 0 to 4 heteroatoms chosen from N, O and S; and
wherein each of the cyclic groups in the moiety $R^6$ is independently optionally substituted by one or more $R^7$ substituents;
$R^7$ represents a group chosen from halogen, alkyl, alkenyl, alkynyl, aryl, arylalkyl, cycloalkyl, heteroaryl, heteroarylalkyl, heterocyclyl, hydroxy, alkylenedioxy, alkoxy, alkylthio, amino, monoalkylamino, dialkylamino, nitro, cyano, oxo, hydroxycarbonyl, alkoxycarbonyl, acylamino, carbamoyl, alkylcarbamoyl, dihydroxyphosphoryloxy and dialkoxyphosphoryloxy groups;
wherein each of the hydrocarbon chains and each of the cyclic moieties in $R^7$ is independently optionally substituted by one or more further $R^8$ substituents;
$R^8$ represents a group chosen from halogen, hydroxy, oxo, cyano, alkyl, difluoromethyl, trifluoromethyl, alkoxy, alkylenedioxy, alkylthio, acylamino, carbamoyl, alkylcarbamoyl, dihydroxyphosphoryloxy, dialkoxyphosphoryloxy, hydroxyalkoxy, phenyl, alkoxycarbonyl, amino, monoalkylamino, dialkylamino, and hydroxycarbonyl groups;
$R^3$ represents a hydrogen or halogen atom, or a nitro, alkoxycarbonyl or alkyl group; wherein the alkyl group is optionally substituted by one or more substituents chosen from hydroxy, alkoxy, alkylthio, amino, monoalkylamino, dialkylamino, hydroxycarbonyl, alkoxycarbonyl, acylamino, carbamoyl and alkylcarbamoyl groups;
$R^4$ represents:
a) hydrogen;
b) a group of formula —$(CH_2)_n$—$R^6$ wherein n is 0, 1 or 2 and $R^6$ is a 5- to 6-membered heteroaryl or heterocyclyl group containing up to 2 heteroatoms chosen from N, O and S, wherein $R^6$ is optionally substituted by a $R^7$ substituent chosen from alkyl, alkoxy, arylalkyl or heteroarylalkyl groups, wherein each of the aryl and heteroaryl moieties of these arylalkyl and heteroarylalkyl $R^7$ substituents is independently optionally substituted by 1 or 2 further $R^8$ substituents chosen from halogen, cyano, alkyl, trifluoromethyl, alkoxy and alkylenedioxy; or
c) an alkyl group, which is optionally substituted by 1 or 2 substituents chosen from amino, monoalkylamino, dialkylamino, —$OR^6$ and —$SR^6$ substituents, wherein $R^6$ is a 5- or 6-membered heteroaryl group containing 1 or 2 heteroatoms, and is optionally substituted by one or more $R^7$ substituents chosen from hydroxy, halogen, amino, monoalkylamino, dialkylamino, cyano, hydroxycarbonyl, alkoxycarbonyl, alkoxy, alkylenedioxy and alkylthio; and wherein the alkyl chains of each of the said monoalkylamino and dialkylamino substituents are independently optionally substituted by 1 or 2 further substituents chosen from a hydroxy group and a group of formula —$(CH_2)_n$—$R^6$, wherein n is an integer from 0 to 4 and $R^6$ is an aryl group;

$R^5$ is hydrogen, a group of formula —$(CH_2)_n R^6$ or a hydrocarbon chain chosen from alkyl, alkenyl and alkynyl, wherein said hydrocarbon chain is optionally substituted by one or more groups chosen from —$(CH_2)_n$—$R^6$ and —O—$(CH_2)_n$—$R^6$;

wherein each $R^6$ is independently a phenyl or a pyridyl group, and wherein each $R^6$ is independently optionally substituted by one or more substituents chosen from halogen, hydroxy, alkyl, alkoxy and alkylthio groups; or an N-oxide or a pharmaceutically acceptable salt thereof.

8. A compound according to claim 1, wherein $R^4$ and $R^5$ form, together with the nitrogen atom to which they are attached, an optionally bridged 5- to 7-membered aromatic or non-aromatic cyclic group, which contains up to two nitrogen atoms, and which is optionally substituted by a group of formula —$(CH_2)_n$—$R^6$ or by a $R^7$ substituent chosen from alkyl, alkenyl and alkynyl chains; wherein each of said alkyl, alkenyl and alkynyl chains is independently optionally substituted by one or more groups of formula —$(CH_2)_n$—$R^6$ or $R^8$ substituents chosen from hydroxy, halogen, alkoxy, alkylthio, amino, monoalkylamino, and dialkylamino groups; wherein each of the alkyl chains in these $R^8$ substituents is independently optionally substituted by one or more further substituents chosen from a group of formula —$(CH_2)_n$—$R^6$, and hydroxy, halogen, alkoxy, alkylthio, amino, monoalkylamino and dialkylamino groups;

wherein each of the $R^6$ groups is independently chosen from each other.

9. A compound according to claim 1, wherein $R^4$ and $R^5$ form, together with the N atom to which they are attached, a 5-, 6- or 7-membered saturated heterocyclic group, which contains 1 or 2 nitrogen atoms and which optionally carries a bridging alkylene group, wherein said saturated heterocyclic cyclic group is optionally substituted by a group of formula —$(CH_2)_n$—$R^6$ wherein n is 0, 1 or 2 and $R^6$ is a 5- or 6-membered aromatic or non-aromatic ring containing 0, 1 or 2 heteroatoms chosen from N, O and S, or by a $R^7$ substituent chosen from alkyl and alkenyl groups, wherein the group $R^6$ is optionally substituted by 1, 2 or 3 further substituents chosen from haloalkyl, alkyl, alkoxy, alkylenedioxy, cyano and halogen groups, and the said $R^7$ substituent optionally substituted by 1 or 2 phenyl substituents.

10. A compound according to claim 1 chosen from:
4-(1,3-Dimethyl-2,4-dioxo-2,3,4,5-tetrahydro-1H-pyrrolo[3,2-d]pyrimidin-6-yl)-N-[2-(pyridin-2-yloxy)ethyl]benzenesulfonamide;
4-(1,3-Dimethyl-2,4-dioxo-2,3,4,5-tetrahydro-1H-pyrrolo[3,2-d]pyrimidin-6-yl)-N-[2-(6 methoxypyridin-2-yloxy)ethyl]benzenesulfonamide;
6-[4-(4-Benzylpiperazine-1-sulphonyl)phenyl]-1,3-dimethyl-1,5-dihydropyrrolo[3,2-d]pyrimidine-2,4-dione;
6-{4-[4-(4-Fluorobenzyl)piperazine-1-sulphonyl]phenyl}-1-methyl-3-propyl-1,5-dihydropyrrolo[3,2-d]pyrimidine-2,4-dione;
6-[4-(4-Benzo[1,3]dioxol-5-ylmethylpiperazine-1-sulphonyl)phenyl]-1-methyl-3-propyl-1,5-dihydropyrrolo[3,2-d]pyrimidine-2,4-dione;
6-{4-[4-(3-Fluorobenzyl)piperazine-1-sulphonyl]phenyl}-1,3-dimethyl-1,5-dihydropyrrolo[3,2-d]pyrimidine-2,4-dione;

1-Methyl-3-propyl-6-[4-(4-pyridin-2-ylpiperazine-1-sulphonyl)phenyl]-1,5-dihydropyrrolo[3,2-d]pyrimidine-2,4-dione,
4-(1,3-Dimethyl-2,4-dioxo-2,3,4,5-tetrahydro-1H-pyrrolo[3,2-d]pyrimidin-6-yl)-N-(2-pyridin-2-ylethyl)benzenesulphonamide;
4-(1-Methyl-2,4-dioxo-3-propyl-2,3,4,5-tetrahydro-1H-pyrrolo[3,2-d]pyrimidin-6-yl)-N-(2-pyridin-2-ylethyl)benzenesulphonamide;
4-(1,3-Dimethyl-2,4-dioxo-2,3,4,5-tetrahydro-1H-pyrrolo[3,2-d]pyrimidin-6-yl)-N-pyridin-2-ylbenzenesulphonamide;
4-(1,3-Dimethyl-2,4-dioxo-2,3,4,5-tetrahydro-1H-pyrrolo[3,2-d]pyrimidin-6-yl)-N-(6-methoxypyridin-3-yl)benzenesulphonamide;
6-{4-[4-(5-Chlorothiophen-2-ylmethyl)piperazine-1-sulphonyl]phenyl}-1,3-dimethyl-1,5-dihydropyrrolo[3,2-d]pyrimidine-2,4-dione;
6-{4-[4-(5-Chlorothiophen-2-ylmethyl)piperazine-1-sulphonyl]phenyl}-1,3-diethyl-1,5-dihydropyrrolo[3,2-d]pyrimidine-2,4-dione;
N-(1-Benzylpiperidin-4-yl)-4-(2,4-dioxo-1,3-dipropyl-2,3,4,5-tetrahydro-1H-pyrrolo[3,2-d]pyrimidin-6-yl)benzenesulphonamide;
4-(1,3-Diethyl-2,4-dioxo-2,3,4,5-tetrahydro-1H-pyrrolo[3,2-d]pyrimidin-6-yl)-N-[1-(4-fluorobenzyl)piperidin-4-yl]benzenesulphonamide;

or a pharmaceutically acceptable salt or an N-oxide thereof.

11. A process for producing a compound of formula I as claimed in claim 1, comprising reacting a sulphonyl chloride of formula II

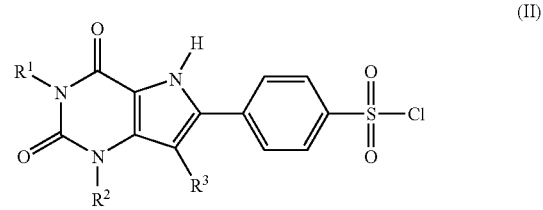

with the corresponding amine III

and optionally converting the product of the reaction into the corresponding N-oxide or pharmaceutically acceptable salt thereof.

12. A process according to claim 11, wherein the sulphonyl chloride of formula II is obtained from the corresponding compound of formula IV:

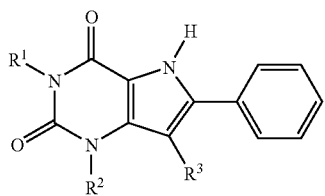

by reaction with an excess of chlorosulphonic acid.

13. A compound of formula II

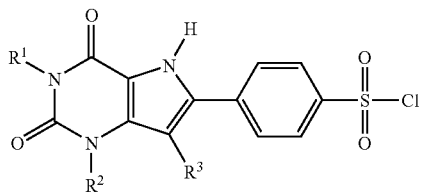

wherein $R^1$ and $R^2$ each independently represents:
- a) a hydrogen atom;
- b) a hydrocarbon chain chosen from an alkyl, alkenyl and alkynyl group, wherein said hydrocarbon chain is optionally substituted by one or more substituents chosen from halogen, hydroxy, alkoxy, alkylthio, amino, monoalkylamino, dialkylamino, cyano, oxo, hydroxycarbonyl, alkoxycarbonyl, acylamino, carbamoyl, alkylcarbamoyl, dihydroxyphosphoryloxy and dialkoxyphosphoryloxy groups; or
- c) a group of formula

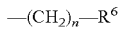

n is an integer from 0 to 4 and $R^6$ represents a 3- to 7-membered aromatic or non-aromatic cyclic group containing from 0 to 4 heteroatoms chosen from N, O and S, wherein said 3- to 7-membered aromatic or non-aromatic cyclic group is optionally bridged and/or fused to another 3- to 7-membered aromatic or non-aromatic cyclic group containing from 0 to 4 heteroatoms chosen from N, O and S;

wherein each of the cyclic groups in the moiety $R^6$ is independently optionally substituted by one or more $R^7$ substituents;

$R^7$ represents a group chosen from halogen, alkyl, alkenyl, alkynyl, aryl, arylalkyl, cycloalkyl, heteroaryl, heteroarylalkyl, heterocyclyl, hydroxy, alkylenedioxy, alkoxy, alkylthio, amino, monoalkylamino, dialkylamino, nitro, cyano, oxo, hydroxycarbonyl, alkoxycarbonyl, acylamino, carbamoyl, alkylcarbamoyl, dihydroxyphosphoryloxy and dialkoxyphosphoryloxy groups;

wherein each of the hydrocarbon chains and each of the cyclic moieties in $R^7$ is independently optionally substituted by one or more further $R^8$ substituents;

$R^8$ represents a group chosen from halogen, hydroxy, oxo, cyano, alkyl, difluoromethyl, trifluoromethyl, alkoxy, alkylenedioxy, alkylthio, acylamino, carbamoyl, alkylcarbamoyl, dihydroxyphosphoryloxy, dialkoxyphosphoryloxy, hydroxyalkoxy, phenyl, alkoxycarbonyl, amino, monoalkylamino, dialkylamino and hydroxycarbonyl groups;

$R^3$ represents a hydrogen or halogen atom, or a nitro, alkoxycarbonyl or alkyl group; wherein the alkyl group is optionally substituted by one or more substituents chosen from hydroxy, alkoxy, alkylthio, amino, monoalkylamino, dialkylamino, hydroxycarbonyl, alkoxycarbonyl, acylamino, carbamoyl and alkylcarbamoyl groups;

or an N-oxide or a pharmaceutically acceptable salt thereof.

14. A pharmaceutical composition comprising a compound as claimed in claim 1 and a pharmaceutically acceptable diluent or carrier.

* * * * *

UNITED STATES PATENT AND TRADEMARK OFFICE
CERTIFICATE OF CORRECTION

PATENT NO. : 7,504,398 B2  
APPLICATION NO. : 10/509280  
DATED : March 17, 2009  
INVENTOR(S) : Vidal Juan et al.

It is certified that error appears in the above-identified patent and that said Letters Patent is hereby corrected as shown below:

On the cover page,

Item [*] Notice: Subject to any disclaimer, the term of this patent is extended or adjusted under 35 U.S.C. 154(b) by (152) days Delete the phrase "by 152 days" and insert --by 308 days--.

In claim 1, column 48, lines 14-15, "$R^6$ being is" should read --$R^6$ is--.

In claim 1, column 48, line 27, "substituents," should read --substituents;--.

In claim 1, column 48, line 40, "sand" should read --and--.

In claim 1, column 49, line 10, "from-$(CH_2)_n$-$R^6$" should read --from -$(CH_2)_n$-$R^6$--.

In claim 7, column 49, line 61, "a) hydrogen" should read --a) a hydrogen--.

In claim 7, column 49, line 62, "b) hydrocarbon" should read --b) a hydrocarbon--.

In claim 9, column 51, line 47, "substituent optionally" should read --substituent is optionally--.

UNITED STATES PATENT AND TRADEMARK OFFICE
CERTIFICATE OF CORRECTION

PATENT NO. : 7,504,398 B2
APPLICATION NO. : 10/509280
DATED : March 17, 2009
INVENTOR(S) : Vidal Juan et al.

It is certified that error appears in the above-identified patent and that said Letters Patent is hereby corrected as shown below:

In claim 10, column 52, lines 1-3, "l-Methyl-3-propyl-6-[4-(4-pyridin-2-ylpiperazine-l-sulphonyl)phenyl]-l,5-dihydropyrrolo[3,2-d]pyrimidine-2,4-dione," should read --1-Methyl-3-propyl-6-[4-(4-pyridin-2-ylpiperazine-1-sulphonyl)phenyl]-1,5-dihydropyrrolo[3,2-d]pyrimidine-2,4-dione;--.

Signed and Sealed this

Twentieth Day of October, 2009

David J. Kappos
*Director of the United States Patent and Trademark Office*